(12) United States Patent
Filho

(10) Patent No.: US 12,070,244 B2
(45) Date of Patent: Aug. 27, 2024

(54) FREE SCAR INSTRUMENT AND METHOD

(71) Applicant: Luiz Lanat Pedreira De Cerqueira Filho, Orlando, FL (US)

(72) Inventor: Luiz Lanat Pedreira De Cerqueira Filho, Orlando, FL (US)

(73) Assignee: Luiz Lanat Pedreira de Cerqueira Filho, Bahia (BR)

( * ) Notice: Subject to any disclaimer, the term of this patent is extended or adjusted under 35 U.S.C. 154(b) by 929 days.

(21) Appl. No.: 16/458,216

(22) Filed: Jul. 1, 2019

(65) Prior Publication Data
US 2020/0015847 A1    Jan. 16, 2020

Related U.S. Application Data

(60) Provisional application No. 62/748,562, filed on Oct. 22, 2018, provisional application No. 62/735,169, (Continued)

(51) Int. Cl.
*A61B 17/34* (2006.01)
*A61B 1/00* (2006.01)
(Continued)

(52) U.S. Cl.
CPC ...... *A61B 17/3423* (2013.01); *A61B 1/00101* (2013.01); *A61B 17/00234* (2013.01); *A61B 17/3439* (2013.01); *A61B 18/085* (2013.01); *A61B 34/30* (2016.02); *A61B 2017/00243* (2013.01); *A61B 2017/00349* (2013.01); *A61B 2017/00398* (2013.01); *A61B 2017/00473* (2013.01); *A61B 2017/00477* (2013.01); *A61B 2017/00734* (2013.01); *A61B 2017/00845* (2013.01); *A61B 17/0469* (2013.01); *A61B 2017/2912* (2013.01); *A61B 2017/2931* (2013.01); *A61B 17/320068* (2013.01); (Continued)

(58) Field of Classification Search
CPC . A61B 1/00101; A61B 34/30; A61B 17/0469; A61B 17/320068; A61B 2017/00398; A61B 2017/00473; A61B 2017/00734; A61B 2017/00845; A61B 2017/2912; A61B 2017/2931
See application file for complete search history.

(56) References Cited

U.S. PATENT DOCUMENTS

2015/0216605 A1 * 8/2015 Baldwin ................ A61B 34/30
                                                        29/428
2015/0272560 A1 * 10/2015 Baldwin ................ A61M 1/84
                                                         606/1
(Continued)

*Primary Examiner* — Brooke Labranche
(74) *Attorney, Agent, or Firm* — Luiz Lanat Pedreira de Cerqueira Filho

(57) ABSTRACT

An invention transfixing a plurality of lumens (28) of a free scar trocar (5) including a plurality of cannulas (5A) space apart by a distance, comprising: two or more elongated rods (3), each including a proximal end (3A) and a distal end (3B); a holder (4); wherein each said proximal end (3A) is connectable to said holder (4) is provided. Also, the invention including at least one protector guide (7); and a functional element (1); wherein each said proximal end (3A) is connectable to said holder (4); wherein each said proximal end (3A) is connectable to said functional element (1) is provided. Methods are provided.

16 Claims, 24 Drawing Sheets

Related U.S. Application Data filed on Sep. 23, 2018, provisional application No. 62/692,793, filed on Jul. 1, 2018.

(51) Int. Cl.
| | |
|---|---|
| *A61B 17/00* | (2006.01) |
| *A61B 18/08* | (2006.01) |
| *A61B 34/30* | (2016.01) |
| *A61B 17/04* | (2006.01) |
| *A61B 17/29* | (2006.01) |
| *A61B 17/32* | (2006.01) |

(52) U.S. Cl.
CPC ............... *A61B 2017/3425* (2013.01); *A61B 2017/3445* (2013.01)

(56) References Cited

U.S. PATENT DOCUMENTS

2018/0161112 A1\* 6/2018 Weir ................. A61B 34/00
2018/0168681 A1\* 6/2018 Kirk .................. A61N 7/02

\* cited by examiner

FREE SCAR INSTRUMENT AND METHOD

CROSS-REFERENCE TO RELATED APPLICATIONS

This application claims an invention which was disclosed in a provisional application number U.S. 62/692,793 filed 2018 Jul. 1, entitled "Surgical instrument of body divided into stems and method.", in application number U.S. 62/735,169 filed 2019 Sep. 23, entitled "Surgical instrument of body divided into stems and method.", and in the application number U.S. 62/748,562 filed 2018 Oct. 22, entitled "Surgical Camera and method". The benefit under 35 USC § 119(e) of the United States provisional application is hereby claimed, and the afore mentioned application is hereby incorporated herein by reference.

DESCRIPTION

Field of Invention

The invention is in the field of medical devices and pertains, particularly, to a surgical instrument 80 to perform surgery without scarring.

Background

In the art of medical devices for performing surgery, many different types of minimally invasive surgical instruments have been developed to perform surgery.

One problem with the traditional minimally invasive surgical instruments is to have a single body with a thick outer diameter that damages the tissue 25. Another problem with the traditional minimally invasive surgical instruments is to require a thickened outer diameter conventional trocar 49 to provide an access lumen 28 to the surgical site 26, the large diameter conventional trocar 49 punctures of the prior art, causing scarring and keloids.

Another limitation of the current minimally invasive surgical instruments is the need for a tissue 25 incision to access the surgical site 26, generally, with the use of a scalpel blade that damages the tissue 25. Another limitation of the current minimally invasive surgical instruments is that the tissue 25 incisions required for the passage of the minimally invasive surgical instruments usually result in scars.

Minimally invasive surgical instruments for performing surgery, such as: robotic surgery, laparoscopic video surgery, thoracoscopic video surgery, video cardiac surgery, video arthroscopic surgery, video urologic surgery, video neurological surgery, video ophthalmologic surgery, orthopedic video surgery, and others, damages the tissue 25 and causes scarring. These scars are not desired because they alter the aesthetics of the body, for example, a professional model, when undergoing gallbladder video surgery, may evolve with unwanted scars from video surgery, which may require restorative plastic surgeries. The possibility of performing a surgery without scarring is a major evolution in surgery.

Therefore, what is clearly needed is a surgical instrument 80 for insertion through a plurality of lumens 28 provided by a free scar trocar 5 including a plurality of cannulas 5A space apart by a distance, that performs the surgery with minimum trauma to the tissue 25, so that tissue 25 healing occurs by the first intention without causing visible tissue 25 scars and a method of use that solves the problems mentioned above.

SUMMARY OF THE INVENTION

In one embodiment of the invention, a surgical device 80 for insertion into a surgical site (26) through a plurality of lumens (28) provided a free scar trocar 5 including a plurality of cannulas 5A space apart by a distance, including: (a) two or more elongated rods 3, each including a proximal end 3A and a distal end 3B; and (b) a holder 4; wherein each said proximal end 3A is connectable to said holder 4; is provided.

Also, in another embodiment, said holder 4 is in connection with said proximal end 3A to transmit at least one of force, power and torque, to said rods 3, is provided.

Also, in another embodiment, said holder 4 is adapted to interchangeably connect to a plurality of external apparatus 27, is provided.

Also, in another embodiment, said proximal end 3A is adapted to interchangeably connect one or more said external apparatus 27, to transmit at least one of force, power and torque, to said rods 3, is provided.

Also, in another embodiment, said rods 3 have an outer diameter adapted to cause minimal trauma to a tissue 25 in order to prevent scarring, are provided.

Also, in another embodiment, at least one of said rods 3 including at least one cavity 9, is provided.

Also, in another embodiment, at least one of said rods 3 is adapted to be in electrical connection with a functional element 1, is provided.

Also, in another embodiment, at least one of said rods 3 works as a tool 8 to perform a surgery, is provided.

Also, in another embodiment, each said distal end 3B further including a piercing tip, is provided.

Also, in another embodiment, the invention further including at least one free scar trocar 5, is provided.

Also, in another embodiment, the invention further including at least one protector guide, is provided.

Also, in another embodiment, said holder 4 further including at least one interconnectable modular part, is provided.

In another embodiment of the invention, a surgical device 80 transfixing a plurality lumen 28 of a free scar trocar 5 including a plurality of cannulas 5A space apart by a distance, including: (a) a plurality of elongated rods 3, each including a proximal end 3A and a distal end 3B; (b) a holder 4; and (c) a functional element 1; each said proximal end 3A is connectable to said holder 4; wherein each said distal end 3B is connectable to said functional element 1, is provided.

Also, in another embodiment, said holder 4 is connectable to at least one external apparatus 27 for a transmission of at least one of force, power and torque, to at least one said elongated rods 3, at least one of said elongated rods 3 is a transmitter of at least one of, force, power and torque, for said functional element 1, is provided.

Also, in another embodiment, said holder 4 is adapted to interchangeably connect to a plurality of external apparatus 27 for the transmission of at least one of force, power and torque, for said rods 3 and for said functional element 1, is provided.

Also, in another embodiment, said holder 4 is operatively connected to at least one of said rods 3 and at least one of said rods 3 is operatively connected to at last one said functional element, is provided.

Also, in another embodiment, at least one of said rods 3 is interchangeable with other rods 3, is provided.

Also, in another embodiment, said functional element 1 is modular, is provided.

Also, in another embodiment, the invention further including an ultrasonic device 27, is provided.

Also, in another embodiment, the invention further including at least one motor 40, is provided.

Also, in another embodiment, the invention further including at least one battery 32, is provided.

Also, in another embodiment, the invention further including at least one video camera, is provided.

Also, in another embodiment, the invention further including at least one camera head 14, is provided.

Also, in another embodiment, the invention further including at least one imager 29 for producing at least one electronic image, is provided.

Also, in another embodiment, the invention further including a surgical stapler 58, is provided.

Also, in another embodiment, said functional element 1 further including a pair of cooperating jaws 10 made to perform a surgical operation, is provided.

Also, in another embodiment, said functional element 1 further including a tool 8 made to perform a surgical operation, is provided.

Also, in another embodiment, said functional element 1 further including a needle holder, is provided.

Also, in another embodiment, said functional element 1 is made to perform a surgical operation, is provided.

Also, in another embodiment, said functional element 1 is adapted to interchangeably connect to another functional element 1, is provided.

Also, in another embodiment, the invention further including at least one modular part, is provided.

Also, in another embodiment, it is adapted to be robotic operating, is provided.

Also, in another embodiment, the invention further including at least one articulation joint 11, is provided.

Also, in another embodiment, the invention further includes the external apparatus 27, is provided.

Also, in another embodiment, said functional element 1 is rotatable around one or more axes, is provided.

Also, in another embodiment, said functional element 1 is modular and detachably connected to said distal end 3B, is provided.

Also, in another embodiment, said functional element 1 includes at least one-part movable with respect to one another in a first plane and said parts are pivotable relative to said distal end 3B of said shaft in said first plane, is provided.

Also, in another embodiment, said distal end 3B is adapted to interchangeably connect to a plurality of said functional elements 1, is provided.

Also, in another embodiment, said holder 4 is adapted to interchangeably connect to a plurality of said external apparatus 27, is provided.

Also, in another embodiment, said holder 4 is adapted to interchangeably connect to a surgical stapler 58, is provided.

Also, in another embodiment, said holder 4 is adapted to interchangeably connect to an ultrasonic device 27F, is provided.

Also, in another embodiment, said holder 4 is adapted to interchangeably connect to a video camera, is provided.

Also, in another embodiment, said holder 4 is detachably connected to said proximal end, is provided.

Also, a method of performing a surgery without scar, including the steps of: (a) inserting a surgical instrument 80 adapted to cause minimal trauma to a tissue 25 into a surgical site 26 through a plurality of transfixations 53 in a tissue 25; (b)transmitting of at least one of force, power and torque for at least one of rods 3 of said surgical instrument80; (c) removing said surgical instrument 80 from tissue 25; is provided.

Also, a method of performing a surgery, the method including the steps of: (a) inserting a plurality of rods 3 of a surgical instrument 80 inside a surgical site 26 through a plurality of transfixations 53 in a tissue 25, each rod 3 including a proximal end 3A and a distal end 3B; (b) connecting a functional element 1 to said distal end 3B inside said surgical site 26; (c) perform a surgery with said surgical instrument; is provided. The method further including, connecting an external apparatus 27 to said proximal end 3A; is provided. The method further including, interchanging said external apparatus 27 with another external apparatus 27; is provided. The method further including, disconnecting said functional element 1 of said distal end 3B, is provided. The method further including, removing said pluralities of rods 3 of said tissue 25; is provided. The method further including, interchanging at least one said interchangeable rod 3F with another said interchangeable rod 3F, is provided. The method further including, interchanging said functional element 1 to another said functional element 1; is provided. The method further including, transfixing a free scar trocar 5 including a plurality of cannulas 5A through a tissue 25 into a surgical site 26 to provide a plurality of transfixations 53; is provided. A method comprising the steps of inserting said elongated rods (3) through the lumen (28); and moving said elongated rods (3) through the lumen; is provided.

DETAILED DESCRIPTION OF THE PREFERRED EMBODIMENTS

The inventor provides a surgical instrument 80 for use through a plurality of lumens 28 provided by a free scar trocar 5 including a plurality of cannulas 5A, the cannulas 5A are space apart by a distance and methods of use. The new invention performs surgery with a minimum of trauma to the tissue 25, so that the tissue 25 healing occurs by first intention without causing visible scarring. The invention is described in enabling detail in the following examples, which may represent more than one embodiment of the invention, together with the accompanying drawings in which, like numerals, represent similar components. Additionally, the structures described herein can be embodied as integrated components or as separate components.

The preferred embodiments according to the invention are shown in FIG. 1-50

Figure 1:
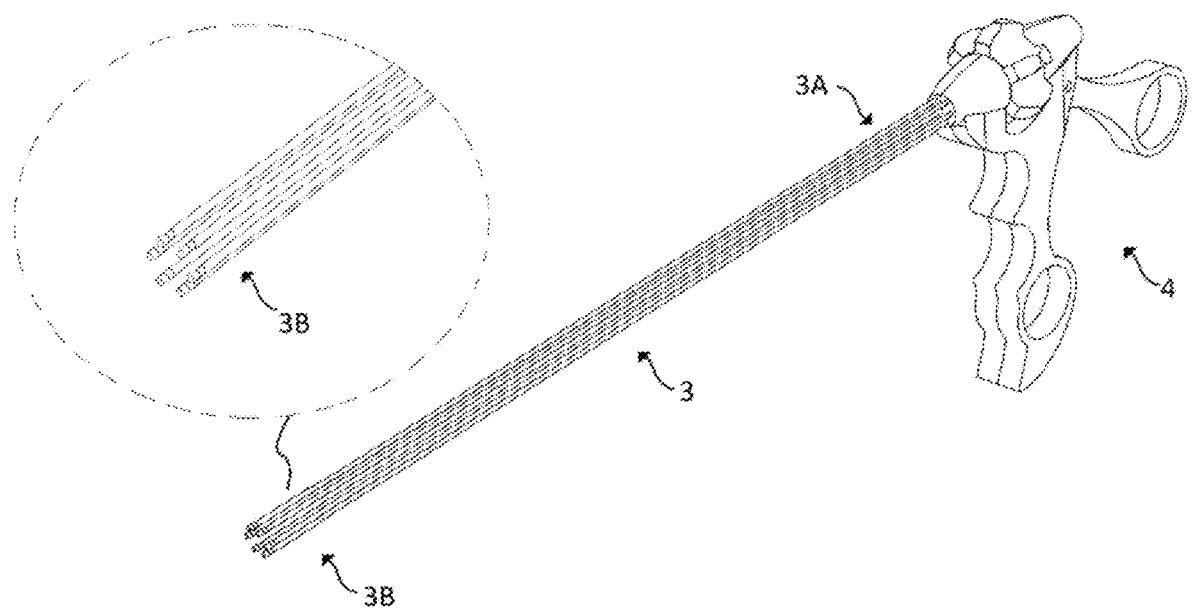
FIG. 1 is a perspective view of one embodiment of the invention, including: six elongated rods 3, the elongated rods 3 including a proximal end 3A and a distal end 3B, and a holder 4 connected to the proximal end 3A.

FIG. 1 is a perspective view of one embodiment of the invention, including: six elongated rods 3, the elongated rods 3 including the proximal end 3A and the distal end 3B, and the holder 4 connected to the proximal end 3A.

One embodiment of the distal end 3B of the plurality of elongated rods 3 is seen in the FIG. 1 in detail. In one characteristic of this embodiment, it is a surgical device for insertion into a surgical site 26 through a plurality of transfixations 53 on a tissue 25. In other characteristic of some embodiment, it is a surgical device for insertion into the surgical site 26 through a plurality of transfixations 53 in a tissue 25 wherein each elongated rod 3 further includes a piercing tip 6 in the distal end 3B to puncture the tissue 25. In other characteristic of some embodiment, it is a surgical device for insertion into the surgical site 26 through a plurality of transfixations 53 in the tissue 25 made by the free scar trocar 5 piercing tip 6. In other characteristic of some embodiment, the piercing tips 6 are adapted to not cause scarring in the tissue 25. Another characteristic of this embodiment is that it is a surgical device for insertion into the surgical site 26 through a plurality of transfixations 53 in the tissue 25 made by the free scar trocar 5. In another characteristic of this embodiment, each the elongated rod 3 have an outer diameter adapted to access the surgical site 26 through lumens 28 provided by the free scar trocar 5 of thin cannulas 5A, the free scar trocar 5 leaves no scar in the tissue 25, the punctures transfixations 53 in the tissue 25 made by the free scar trocar 5 cannulas 5A piercing tips 6 heals by first intention and leaves no visible scars on the tissue 25. In another characteristic of this embodiment, the holder 4 is a single piece, and is configured to be manually operating. In other characteristic this embodiment, it is a functional surgical instrument 80 for use in surgery. In another characteristic this embodiment, it is a surgical manipulator with the function of raising intestinal loops, moving away live structures and assisting in surgeries.

Figure 2:
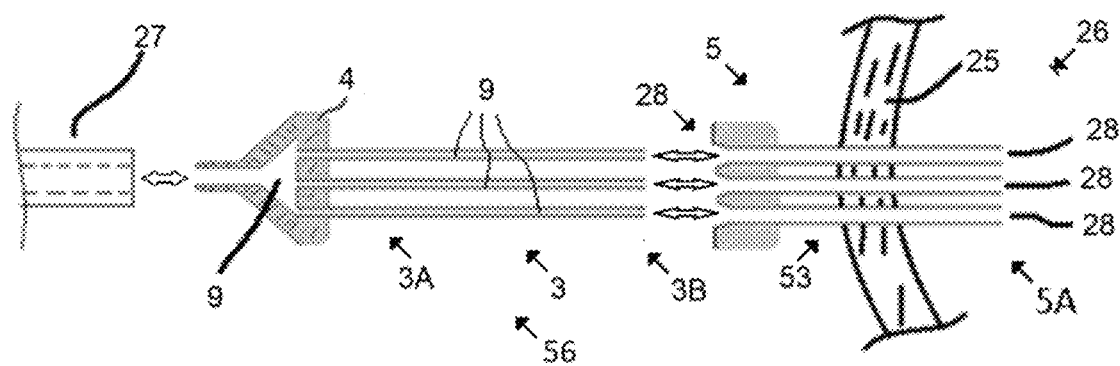
FIG. 2 is a perspective view of other embodiment of the invention, including: three elongated rods 3, the elongated rods 3 including the proximal end 3A and the distal end 3B, and the holder 4 connected to the proximal end 3A.

FIG. 2 is a perspective view of other embodiment of the invention, including: three elongated rods3, the elongated rods 3 including the proximal end 3A and the distal end 3B, and the holder 4 connected to the proximal end 3A.

One characteristic of this embodiment is to further comprise a cavity 9 as an access of liquids, gases and debris through the elongated rods 3 and through the holder 4. One characteristic of this embodiment is that each elongated rod 3 has the cavity 9, the holder 4 also has the cavity 9. In another characteristic of this embodiment, the elongated rods 3 are tubes including the cavity 9.

In another characteristic of this embodiment, the free scar trocar 5 including three cannulas 5A is providing three lumens 28 to the surgical site 26 through the tissue 25. In another characteristic of this embodiment, it is adapted to be inserted into the free scar trocar 5 with three lumens 28 through the tissue 25 to a surgical site 26. In other characteristic of this embodiment, the punctures transfixations 53 in the tissue 25 made by the free scar trocar 5 heals by first intention and leaves no visible scars on the tissue 25. In other characteristic of this embodiment, after the surgery, the free scar trocar 5 is adapted to be removed from the tissue 25. In another characteristic of this embodiment, the elongated rods 3 are adapted to be inserted through the three lumens 28, provided by the free scar trocar 5, to access the surgical site 26. Other characteristic of some the embodiments is that each of the elongated rods 3 has an outer diameter adapted to be inserted through the free scar trocar 5 including a plurality cannulas 5A, and to cause minimal trauma to the tissue 25 in order to prevent scarring. This embodiment is ready to be inserted into the three lumens 28 of the free scar trocar 5. In other characteristic this embodiment is adapted to operatively connect to an external apparatus 27. In another characteristic of this embodiment, the external apparatus 27 is a vacuum hose 271 for aspiration of liquids from the surgical site 26 by the cavity 9. The larger arrow indicates the direction in which the vacuum hose 271 connects in the holder 4. In other characteristic of this embodiment, the elongated rods 3 are made of a rigid material.

Another characteristic of this embodiment is its function of aspirating liquids and debris contents from the surgical site 26.

Another characteristic of some embodiments is to be a surgical irrigator for irrigating the surgical site 26 with serum, blood and medicaments, but is not limited to them. Another characteristic of some embodiment is to be a surgical drain 56 for aspiration of liquids and debris contents within the surgical site 26. In other characteristic of this embodiment, the number of elongated rods 3 are not limited to them. In another characteristic of some embodiments, the elongated rods 3 are made of a flexible material but is not limited to them. In another characteristic of some embodiments, at least one elongated rod 3 has the cavity 9. In another characteristic of some embodiments, the holder 4 does not have the cavity 9. In other characteristic of some embodiment, the elongated rods 3 are made of a flexible material, the distal end 3B is adapted to facilitate the drainage of liquids from the surgical site 26 including, at least one of, lateral perforations, sulcus, but is not limited to them. Another characteristic of some embodiments is to be a surgical drain 56 for draining the surgical site 26 with serum, blood, and medicaments, but is not limited to them. Another characteristic of some embodiments is a surgical drain 56 for draining the surgical site 26 with serum, blood, and medicaments, made of elastic material, for example: silicone and latex, but is not limited to them.

Figure 3:
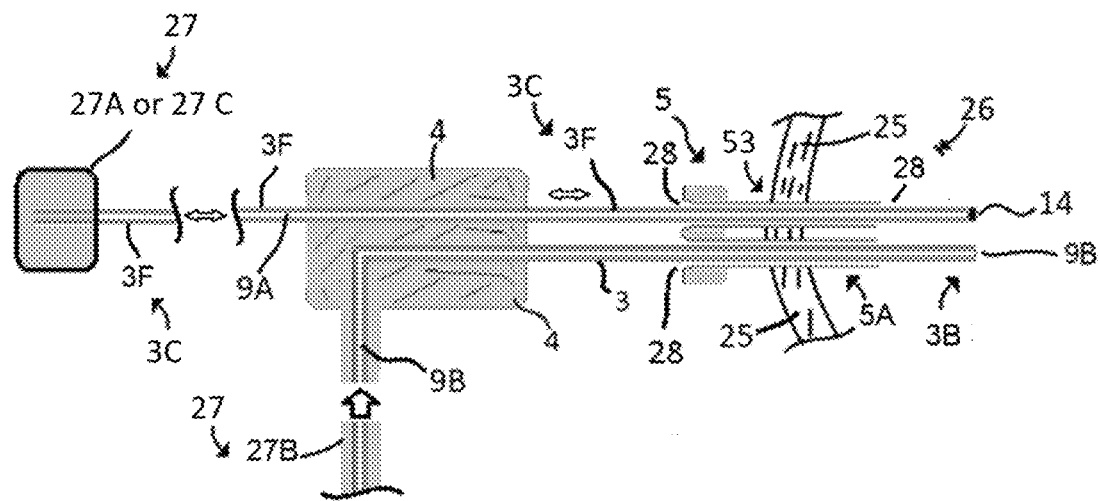
FIG. 3 is a perspective view of another embodiment of the invention, including two elongated rods 3.

FIG. 3 is a perspective view of another embodiment of the invention, including two elongated rods 3.

The two elongated rods 3 are inserted in two lumens 28 of the free scar trocar 5, the free scar trocar 5 provides two lumens 28 for the elongated rods 3 to access the surgical site 26, the distal ends 3B are inside the surgical site 26, the distal ends 3B extend into the interior of the surgical site 26.

In another characteristic of this embodiment, at least one of the elongate rods 3 functions as an interchangeable rod 3F for the transmission of at least one of force, power and torque, the distal end 3B includes a camera head 14.

In another characteristic of this embodiment, electrical wires 52 are placed extending through cavity 9A. In other characteristic of this embodiment, the camera head 14 electronics includes an imager 29 (it is not shown in the drawing) for producing an electronic image, and a battery 32 (it is not shown in the drawing).

In another characteristic, this embodiment is adapted to operatively connect to at least one external apparatus 27, including: an image processor 27A, the video camera 27C, and the light source 27B.

In other characteristic of this embodiment, the electrical wires 52 (it is not shown in the drawing) are adapted to connect the camera head 14 to the external apparatus 27, which is the image processor27A. In another characteristic of this embodiment, the image is adapted to be displayed on a video monitor (it is not shown in the drawing). In other characteristic of this embodiment, the image processor 27A is a control circuitry for processing the electronic image as produced by the imager 29.

In another characteristic of this embodiment, the imager 29 is for image pickup. Also, in another characteristic of this embodiment, the electrical wires 52 in the cavity 9A communicate the imager 29 with the external apparatus 27A. In another characteristic of this embodiment, the imager 29 is adapted to connect to the electrical wires 52.

In another characteristic of some embodiment, the imager 29 is a solid-state imager 29. In another characteristic of some embodiment, the imager 29 is a CCD imager 29. In another characteristic of some embodiment, the imager 29 is a CMOS imager 29. In other characteristic of some embodiment, the imager 29 and the camera head 14 electronics are configured on a single chip. In other characteristic of some embodiment, the imager 29 produces an electronic image upon being actuated by the image processor 27A control circuitry.

In another characteristic of some embodiment, the cavity 9A includes a first optical path 13. In another characteristic of some embodiment, the first optical path 13A extends through the cavity 9A.

In another characteristic of some embodiment, a second optical path 13B extends through the cavity 9B.

In another characteristic of some embodiment, the elongated rod 3 includes the second optical path 13B to illuminate the surgical site 26. In other characteristic of some embodiment, the second optical path 13B has optical fibers that pass through the cavity 9B. In other characteristic of some embodiment, the second optical path 13 B is implemented with a liquid light guide. In other characteristic of some embodiment, the cavity 9B of the command rod 3C include the optical path 13 extending from the light source 27B to the camera head 14.

In other characteristic of some embodiment, the external apparatus 27 includes the light source 27B. In other characteristic of some embodiment, the light source 27B connects to the existing optical fibers of the second optical path 13B that pass inside the cavity 9B to illuminate the surgical site 26. In one characteristic of some embodiments, there are two optical paths 13 to illuminate the surgical site 26. In one characteristic of some embodiments, there are three optical paths 13 to illuminate the surgical site 26, but the number of optical paths 13 to illuminate the surgical site 26 is not limited to them. In one characteristic of some embodiment, the number of command rods 3C used to illuminate the surgical site 26 is not limited to them.

In another characteristic of some embodiment, it includes optical lenses 15 (it is not shown in the drawing). In another characteristic of some embodiment, the cavity 9A has optical lenses 15 for transmitting images of the surgical site 26 to an external apparatus 27A. In another characteristic of some embodiment, the cavity 9A has optical lenses 15 for transmitting images of the surgical site 26 to the video camera 27C. Another characteristic of some embodiment is to capture the images of the optical lenses 15 of the cavity 9 with an interchangeable rod 3F, which is the camera 14, and display the images of the surgical site 26 on a monitor. Another characteristic of some embodiment is to capture the images of the optical lenses 15 of the cavity 9 with an external camera head 14.

In one characteristic of some embodiments, there are two command rods 3C including the two imager 29. In one characteristic of some embodiments, there are three command rods 3C including three imagers 29, but the number of command rods 3C including the imagers 29 are not limited to them. In one characteristic of some embodiments, the cavity 9B has wires to transmit electrical power to a lighting emission diode, LED 51, locate in the distal end 3B of the command rod 3C for the purpose of illuminating de surgical site 26.

Figure 4:
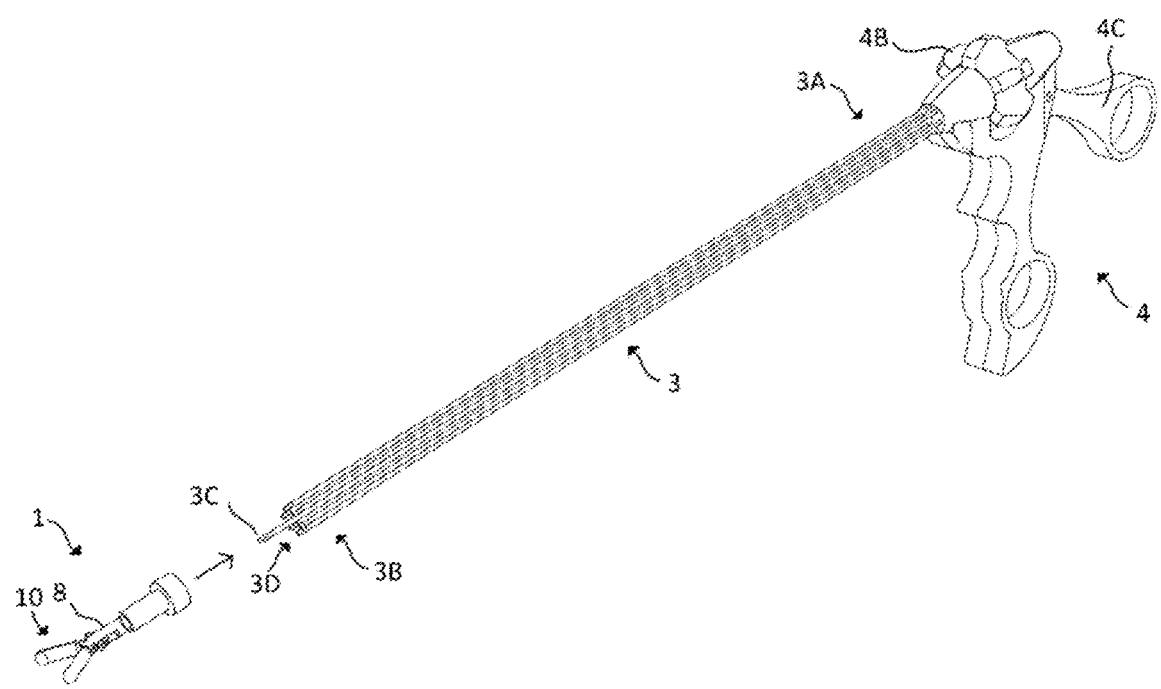
FIG. 4 is a perspective view of another embodiment of the invention, including: seven elongated rods 3.

FIG. 4 is a perspective view of another embodiment of the invention, including: seven elongated rods 3. In this embodiment, the elongated rods 3 include the proximal end 3A and the distal end 3B, the holder 4 connected to the proximal end 3A and the functional element 1 is detachably connected to the distal end 3B. In another characteristic of this embodiment, the holder 4 includes a spinner 4B and a lever 4C. In other characteristic of this embodiment, the holder 4 is not modular, and the holder 4 is connected to the proximal end 3A in a not disconnecting manner. In another characteristic of this embodiment, the functional element 1 is completely detachable from the distal end 3B, the arrow shows the direction in which the functional element 1 connects to the distal end 3B. In another characteristic of this embodiment, the holder 4 is configured to be manually operating. In another characteristic of this embodiment, the holder 4 is adapted to use the command rods 3C to control the functional element 1. One characteristic of this embodiment is that one command rod 3C is operatively connected to the functional element 1. In another characteristic of this embodiment, the command rod 3C is a transmission member, at least one of, force, power and torque to the functional element 1.

In another characteristic of this embodiment, six support rods 3D are connecting the functional element 1 with the support function.

In another characteristic of this embodiment, the functional element 1 is rotatable around its own axis. In another characteristic of this embodiment, the spinner 4B is operably connected to the elongated rod 3C. In another characteristic of this embodiment, manually rotating the spinner 4B causes the rotation of the command rod 3C that rotates the functional element 1.

In other characteristic of this embodiment, the functional element 1 is made to perform a surgical operation. In another characteristic of this embodiment, the functional element 1 further includes the tool 8. In other characteristic of this embodiment, the tool 8 includes a pair of cooperating jaws 10 made to perform a surgical operation. In other characteristic of this embodiment, a lever 4C is operably connected to the command rod 3C. In other characteristic of this embodiment, the longitudinal movement of the lever 4C is transmitted to the command rod 3C. In other characteristic of this embodiment, the longitudinal movement of the command rod 3C is transmitted to the functional element 1 by the command rod 3C. In other characteristic of this embodiment, the longitudinal movement of the command rod 3C opens and closes the pair of jaws 10 of the functional element 1. In another characteristic of this embodiment, the holder 4 is configured to be manually operating.

In another characteristic of this embodiment, the distal end 3B is adapted to interchangeably connect to a plurality of the functional elements 1. In another characteristic of this embodiment the functional element 1 is adapted to be interchangeably connected to another functional element 1.

In one characteristic of some embodiments, the functional element 1 includes the tool 8 to perform a surgery operation. In some embodiments, the tool 8 is an ultrasonic scissors; in some embodiments, the tool 8 is a camera heard 14; in some embodiments, the tool 8 is a tweezer 54; in some embodiments, the tool 8 include a suture device 55; in some embodiments the tool 8 is scissors; in some embodiments the tool 8 include a surgical stapler 58; in some embodiments the tool 8 includes a stapler 58 loading 59; in some embodiments the tool 8 is a clamp 60; in some embodiments the tool 8 is a linkage mechanism; in some embodiments the tool 8 includes an electrical device 62, in some embodiments the tool 8 includes a motor 40; in some embodiments the tool 8 includes a solenoid 64; in some embodiments the tool 8 includes an electric scalpel 65; in some embodiments the functional element 1 includes an ultrasonic scissors; in some embodiments the functional element 1 includes an ultrasonic device 27F; in some embodiments the functional element 1 includes a retractor 67; in some embodiments the functional element 1 includes a vacuum cleaner 68; in some embodiments the functional element 1 includes an optics 69; in some embodiments the functional element 1 includes a suture device 55; in some embodiments the functional element 1 includes a needle-holder 70: in some embodiments the functional element 1 includes a laser 71; in some embodiments the functional element 1 includes a bag 72; in some embodiments the functional element 1 includes a robot; in some embodiments the functional element 1 includes servomechanism; in some embodiments the functional element 1 includes a motor 40; in some embodiments the functional element 1 includes a servo-motor40, but is not limited to them.

Figure 5:
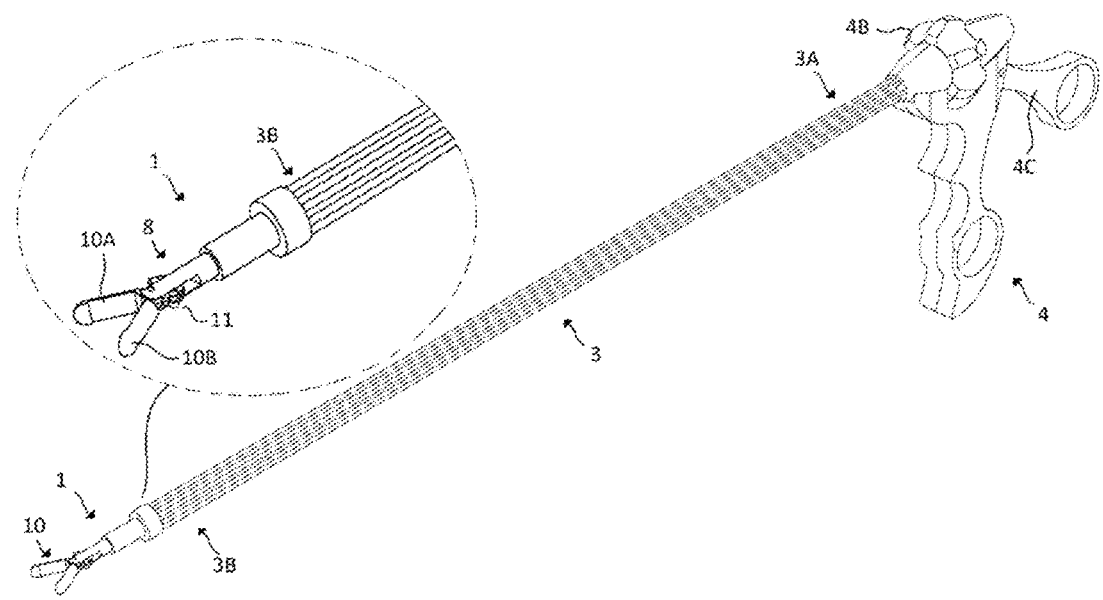
FIG. 5 is a perspective view of another embodiment of the invention, including: five elongated rods 3.

FIG. 5 is a perspective view of another embodiment of the invention, including: five elongated rods 3. In this embodiment, the elongated rod 3 including the proximal end 3A and the distal end 3B, the holder 4 connected to the proximal end 3A, and the functional element 1 detachably connected to the distal end 3B. One embodiment of the distal end 3B and the functional element 1 are seen in detail in the FIG. 5.

In another characteristic of some embodiment, the holder 4 is not modular, and the holder 4 is connected to the proximal end 3A in a non-disconnecting manner. In another characteristic of this embodiment, the functional element 1 is connected to the distal end 3B.

In another characteristic of some embodiments of the invention, the elongated rod 3 connects the holder 4 to the functional element 1. In another characteristic of this embodiment, the holder 4 is adapted to actuate the functional element 1 via the command rod 3C (it is not shown in the drawing). In another characteristic of this embodiment, the holder 4 includes the spinner 4B and the lever 4C. In one characteristics of this embodiment, the spinner 4B is connected to the command rod 3C (it is not shown in the drawing). In other characteristic of this embodiment, the functional element 1 is adapted to be rotated relative to the longitudinal axis from the rotation of the spinner 4B. In another characteristic of this embodiment, the command rod 3C is connected to the functional element 1, the rotation of the command rod 3C causes the functional element 1 to rotate. In another characteristic of this embodiment, the spinner 4B rotates causes the command rod 3C to rotate the functional element 1.

In other characteristic of this embodiment, the functional element 1 comprises a pair of cooperating jaws 10 made to perform a surgical operation. In another characteristic of this embodiment, the functional element 1 comprises an articulation joint 11, to open and close the jaws 10. In other characteristic of this embodiment, the functional element 1 is detachably connected to the command rod 3C.

In one characteristics of this embodiment, the longitudinal movement of a lever 4C, the opening and closing of the lever 4C, causes a longitudinal movement of the command rod 3C, this movement opens or closes the pair of jaws 10 of the functional element 1.

In another characteristic of this embodiment, the functional element 1 is adapted to interchangeably connect to another functional element 1. In another characteristic of this embodiment, the functional element 1 is adapted to be disconnected from the distal end 3B and another functional element 1 is adapted to be connected to the distal end 3B.

In another characteristic of this embodiment, the functional element 1 includes a gripper tool 8. In another characteristic of this embodiment, the tool 8 includes two cooperative jaws 10, jaw 10A and jaw 10B. In other characteristic of this embodiment, the command rod 3C connects to the functional element 1 to activate a mechanism to open and close the pair of jaws 10.

In other characteristic of some embodiment, that command rod 3C is a transmission member of force to open and close the pair of jaws 10 of the gripper 74. Also, the same command rod 3C is a transmission member of torque to rotate the functional element 1 in relation to the elongated rods 3 longitudinal direction.

In one characteristic of some embodiments, at least one the elongated rods 3 is a transmission member, at least one of, force, power and torque. In one characteristic of some embodiments, other command rods 3C may function to activate a mechanism in the functional element 1 from the holder 4, for example: a button on the holder 4 that disconnects the functional element 1.

In some embodiments, the holder 4 is adapted to use the command rod 3C to control the functional element 1.

Figure 6:
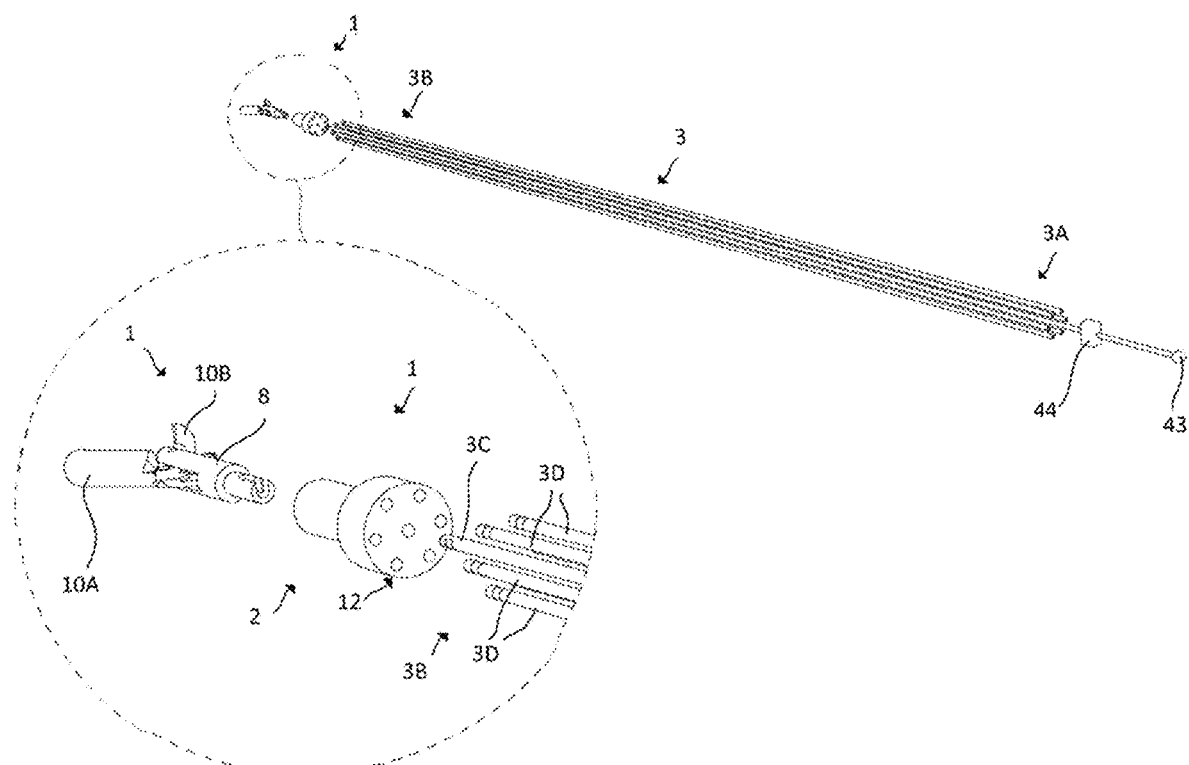
FIG. 6 is a perspective view of the elongated rod 3 and a functional element 1, according to another embodiment of the invention.

FIG. 6 is a perspective view of the elongated rods 3 and the functional element 1, according to another embodiment of the invention.

In this example, the holder 4 is not displayed, the functional element 1 is disconnected from the distal end 3B. In other characteristic of this embodiment, the command rod 3C is longer than the support rod 3D to connect a base 44 to the spinner 4B. In another characteristic of this embodiment, the base 44 of the command rod 3C connects to the spinner 4B to rotate the command rod 3C and this rotates the functional element 1.

In another characteristic of this embodiment, a boll 43 connects to the lever 4C to act on the functional element 1. In this example, the functional element 1 includes the tool 8 and the adapter 2. In this example, the command rod 3C extends beyond the proximal end 3A. In other characteristic of this embodiment, the command rod 3C is adapted to connect to the holder 4. In this example, the command rod 3C is ready to connect to a tool 8 and the support rods 3D are ready to connect to housings 12.

Figure 7:
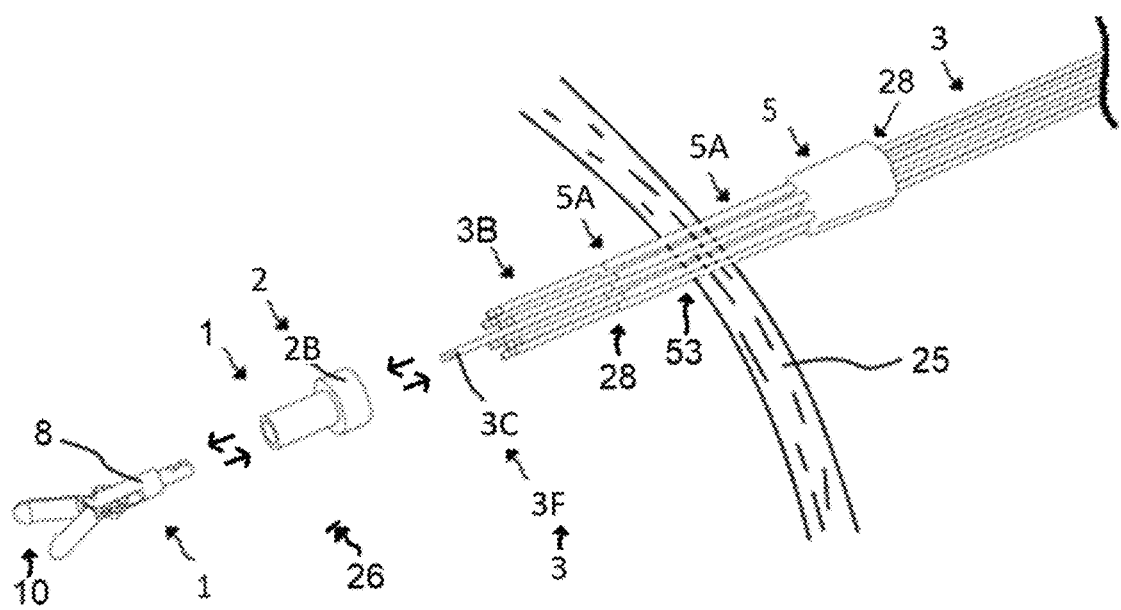
FIG. 7 is a perspective view of another embodiment of the invention with the functional element 1 within a surgical site 26.

FIG. 7 is a perspective view of another embodiment of the invention, the functional element 1 is within the surgical site 26. This example is another embodiment of the surgical device for insertion into the surgical site 26 through a plurality of transfixations 53 in the tissue 25. In another characteristic of this embodiment, one part of the plurality of elongated rods 3 are seen, the plurality of elongated rods 3 are transfixing the tissue 25 through the plurality of lumens 28 of the free scar trocar 5, the distal end 3B is inside the surgical site 26.

In this example, the functional element 1 is ready to be connected to the distal end 3B inside the surgical site 26. In another characteristic of this embodiment, the functional element 1 is modular, including the adapter 2 and the tool 8.

In this example, the adapter 2 is disconnected from the distal end 3B, the tool 8 is disconnected from the adapter 2. In other characteristic of this embodiment, the elongated rod 3 passes through the insides the lumen 28 of the free scar trocar 5 to access the surgical site 26. In this example, the free scar trocar 5 includes the cannulas 5A. In other characteristic of some embodiment, the free scar trocar 5 has the cannulas 5A made to be inserted into the surgical site 26 through a plurality of transfixations 53 in the tissue 25 without causing scarring. In other characteristic of this embodiment, the free scar trocar 5 is adapted to transfix the tissue 25 without scarring. In another characteristic of this embodiment, the cannulas 5A have an external diameter sufficiently thin to avoid causing scars on the tissue 25. In this example, the elongated rod 3 passes through the lumens 28 of the free scar trocar 5, through the lumen 28 of the cannulas 5A. In this example, the distal end 3B is free to connect to the adapter 2, the adapter 2 is ready to be inserted into the distal end 3B of the elongated rods 3, and the tool 8 is ready to be inserted into the adapter 2. In other characteristic of this embodiment, the invention is interchangeably on the functional element 1 with another functional element 1. In another characteristic of this embodiment, the tool 8 is adapted to be disconnected from the adapter 2 and replaced by another tool 8. In another characteristic of this embodiment, the adapter 2 is adapted to be disconnected from the distal end 3B and replaced by another adapter 2. In one characteristic of some embodiments, the functional element 1 is modular, including a plurality of detachably connected parts. In one characteristic of some embodiments, the free scar trocar 5 is part of the invention. In some embodiments, the invention further comprises at least one free scar trocar 5.

Figure 8:
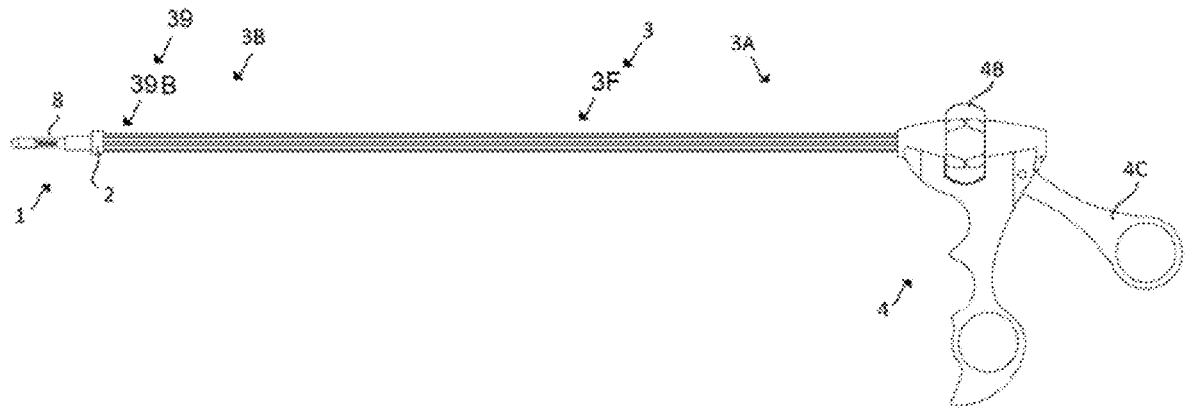
FIG. 8 is a lateral view of the invention for manual use according to another embodiment of the invention.

FIG. 8 is a lateral view of the invention for manual use according to another embodiment of the invention.

In another characteristic of this embodiment, the functional element 1 is connectable to the distal end 3B. In another characteristic of this embodiment, the holder 4 includes the spinner 4B and the lever 4C. In other characteristic of this embodiment, the holder 4 is not modular and the holder 4 is connected to the proximal end 3A in a non-disconnecting manner.

Figure 9:
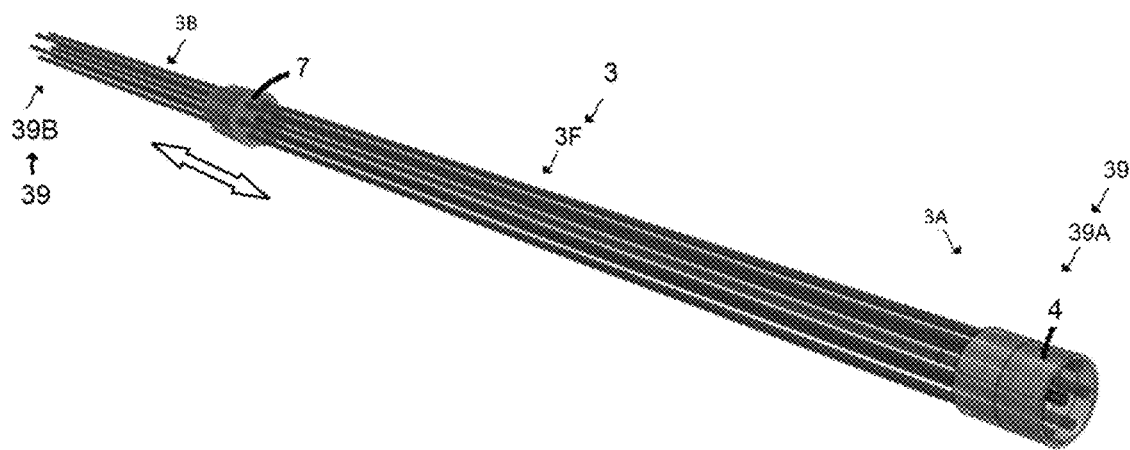
FIG. 9 is a perspective view of another embodiment of the invention, including a protector guide 7.

FIG. 9 is a perspective view of another embodiment of the invention, including the protector guide 7. This embodiment is another example of a surgical device for insertion into the surgical site 26 through a plurality of lumens 28 provided by a free scar trocar 5 including a plurality of cannulas 5A space apart by a distance, including: a plurality of elongated rods 3, the elongated rods 3 including proximal ends 3A and distal ends 3B, and the holder 4 connectable to the proximal end 3A, further including the protector guide 7.

In another characteristic, this embodiment includes seven elongated rods 3. In another characteristic of some embodiment, the holder 4 is connectedly fixed to the proximal end 3A.

In another characteristic of this embodiment, the holder 4 is adapted to interchangeably connect to a plurality of external apparatus 27 for the transmission of, at least one of, force, power and torque, for the elongated rod 3. In another characteristic of this embodiment, the holder 4 is adapted to functionally connect the plurality of external apparatus 27. In another characteristic of this embodiment, the elongated rods 3 are adapted to work as the support rod 3D and the command rod 3C according on the external apparatus 27 to connect. In another characteristic of this embodiment, the embodiment has six support rods 3D and one command rod 3C. In another characteristic of some embodiments, the holder 4 is adapted to slide on the elongated rod 3 along the length of the elongated rod 3 or by a segment of the elongated rod 3. In another characteristic of some embodiments, the elongated rods 3 are solid. In another characteristic of some embodiments, the elongated rods 3 have the cavity 9. In another characteristic of some embodiments, through the cavity 9 of the elongated rods 3, passes a nuclear rod 3E. In other characteristics of some embodiments, a nuclear rods 3E are structures for: power transmission, torque transmission and force transmission, for example: electrical connection, cables, rods, hydraulic structures, but is not limited to them.

In another characteristic of this embodiment, the distal end 3B is adapted to interchangeably connect to a plurality of the functional elements 1.

In another characteristic of this embodiment, at least one of the elongated rods 3 is an interchangeable rod 3F interchangeable with another interchangeable rod 3F. In another characteristic of this embodiment, each elongated rod 3 has a specific function, for example: during the procedure, the interchangeable rod 3F with a mechanical function is adapted to be replaced by the interchangeable rod 3F with a hydraulic function, the interchangeable rod 3F is adapted to be removed and replaced by another interchangeable rod 3F. In other characteristic of some embodiment, the command rod 3C has a hydraulic mechanism, or a mechanical mechanism, or an electrical mechanism, but it is not limited to them. Some interchangeable rod 3F are adapted to be replaced and connected to another external devices 27 and to another functional elements 1. In other characteristic of some embodiment, there is an auxiliary device for the replacement. In other characteristic of some embodiment, during a procedure, at least one interchangeable rod 3F is adapted to be removed from the plurality of interchangeable rod 3F and replaced with another interchangeable rod 3F.

In one characteristic of some embodiments, there is a mechanism for releasing the holder 4, the holder 4 is adapted to be detached and replaced. In one characteristic of some embodiments, the holder 4 is adapted to move longitudinally on the elongated rod 3.

Figure 10:
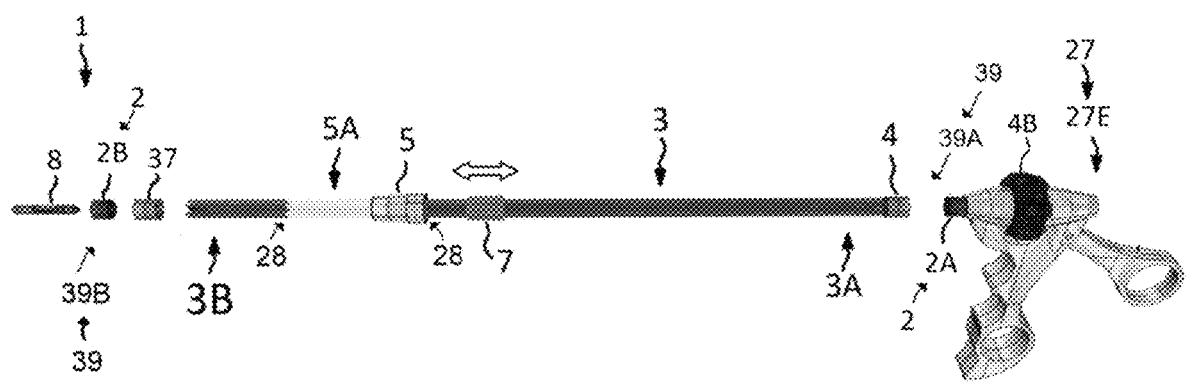
FIG. 10 is a perspective view of another embodiment of the invention including a free scar trocar 5 and the protector guide 7.

FIG. 10 is a perspective view of another embodiment of the invention including the free scar trocar 5 and the protector guide 7.

This embodiment is modular, the handler 27E is detachably connected to the holder 4, and the functional element 1 is detachably connected to the distal end 3B. In another characteristic of this embodiment, the functional element 1 is modular including the connector 37B, the adapter 2B, and the tool 8. This embodiment includes eight elongated rods 3, the eight elongated rods 3 including proximal ends 3A and distal ends 3B and the free scar trocar 5. In another characteristic, this embodiment further includes a modular functional element 1 detachably connected to the distal end 3B. In another characteristic of this embodiment, the functional element 1 is interchangeable with another functional element 1 and other axle assemblies and surgical instruments, the functional element 1 is adapted to be disconnected and connected to another type of functional element 1.

In another characteristic of this embodiment, the free scar trocar 5 includes eight cannulas 5A. In other characteristic of this embodiment, the holder 4 is adapted to connect to an external apparatus 27 for the transmission of, at least one of, force, power and torque, for the functional element 1. In other characteristic of this embodiment, the external apparatus 27 is the handler 27E adapted for manual operation. In other characteristic of this embodiment, the modular functional element 1 is made to perform a surgical operation.

In another characteristic of this embodiment, the holder 4 is detachably connected to the external apparatus 27.

In another characteristic of this embodiment, the holder 4 is completely detachable from the handler 27E. In another characteristic of this embodiment, the handler 27E is operatively connectable to the holder 4 by the adapter 2A. In another characteristic of this embodiment, the handler 27E is configured to be manually operating.

In another characteristic of this embodiment, a protector guide 7 is detachably connectable to the free scar trocar 5. In one characteristic of some embodiments, the holder 4 is modular, including detachable connected parts.

Figure 11:
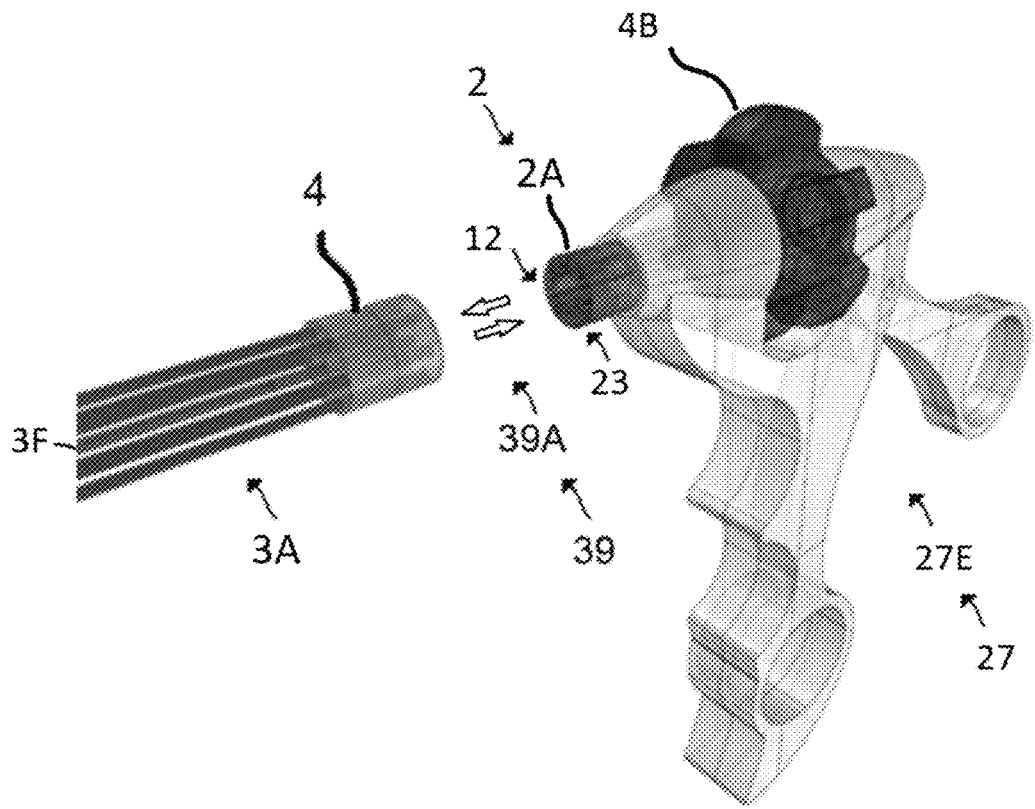
FIG. 11 is a perspective view of the proximal end 3A, the holder 4 and a handler 27E, according to another embodiment of the invention.

FIG. 11 is a perspective view of the proximal end 3A, the holder 4 and the external apparatus 27, according to another embodiment of the invention.

In another characteristic of this embodiment, the holder 4 is adapted to connect to at least one external apparatus 27 for the transmission of, at least one of, force, power and torque, for the functional element 1.

In another characteristic of this embodiment, the proximal end 3A is adapted to interchangeably connect to a plurality of the external apparatus 27.

In another characteristic of this embodiment, the holder 4 is adapted to interchangeably connect to a plurality of the external apparatus 27.

In another characteristic of this embodiment, the holder 4 is operatively connectable to at least one of the elongated rods 3 and at least one of the command rods 3C and is operatively connectable to the adapter 2A.

In another characteristic of this embodiment, the command rods 3C are functionally connectable to the holder 4 and functionally connectable to the adapter 2A.

In another characteristic of this embodiment, at least one of the command rods 3C is a transmitter of, at least one of, force, power and torque, for the adapter 2A. In another characteristic of this embodiment, the holder 4 is adapted to interchangeably connect to a plurality of external apparatus 27 for the transmission of, at least one of, force, power and torque, for the command rod 3C and for the functional element 1.

In another characteristic of some embodiment, the external device 27 further includes at least one motor 40. In another characteristic of some embodiment, the external device includes one battery 32. In another characteristic of some embodiment, it is connectable to the external device 27 including a surgical stapler 58. In another characteristic of this embodiment, it is connectable to the external device 27 including the light source 27B. In another characteristic of some embodiment, it is connectable to the external device 27 including the robotic arm 27D. In another characteristic of some embodiment, it is connectable to the external device 27 including the ultrasonic device 27F. In another characteristic of some embodiment, it is connectable to the external device 27 including a surgical robot 27H. In another characteristic of some embodiment, it is connectable to the external device 27 including a laser device 27J. In another characteristic of some embodiment, it is connectable to some external device 27 including a servo motor 40. In another characteristic of some embodiment, it is connectable to the external device 27 including an electric source 27L. In another characteristic of some embodiment, it is connectable to the external device 27 including a power source 27M. In another characteristic of some embodiment, it is connectable to the external device 27 including the ultrasonic generator 35 but is not limited to them.

In another characteristic of this embodiment, the functional element 1 is made to perform a surgical operation. In another characteristic of this embodiment, the holder 4 is detachably connected to the proximal end 3A. In another characteristic of this embodiment, the interchangeable rod 3F are interchangeable with other interchangeable rod 3F. In some embodiments, the surgical stapler 58 is adapted to be robotic operating.

In one characteristic of some embodiments, the surgical stapler 58 manipulator is modular, including detachable connectable parts. In one characteristic of some embodiments, the battery 32 is a detachable connectable modular part.

In one characteristic of some embodiments, the surgical stapler 58 manipulator 27 G includes a servo motor, a motor 40 or a linear actuator to actuate at least one of the command rods 3C.

In one characteristic of some embodiments, the surgical stapler 58 manipulator 27G includes at least one battery 32. In one characteristic of some embodiments, the surgical stapler 58 manipulator 27G is a supplier member, at least one of, force, power and torque to, at least, one elongated rod 3. In some embodiments the invention includes the external apparatus 27.

Figure 12:
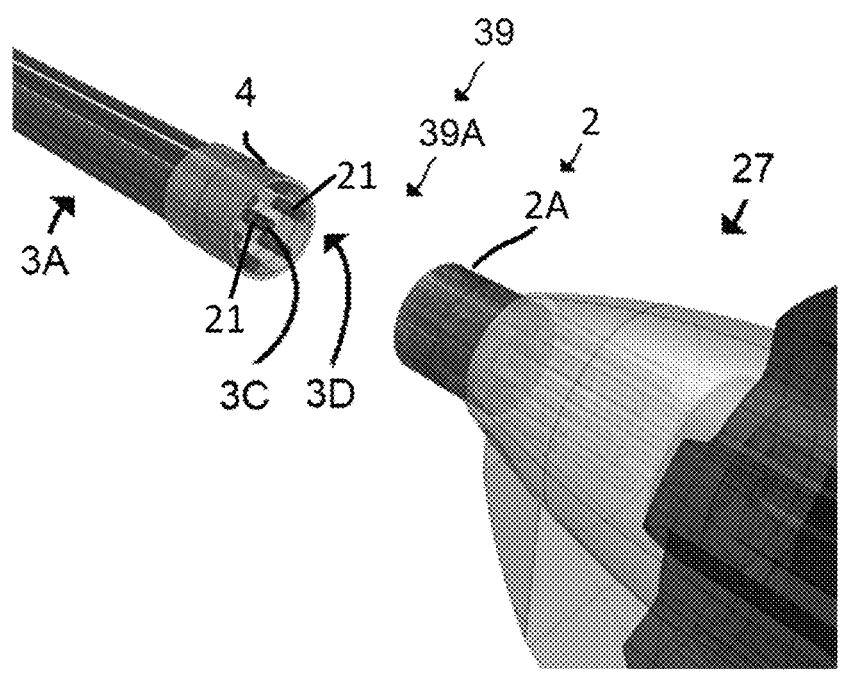
FIG. 12 is a perspective view of the proximal end 3A, the holder 4 and an external apparatus 27, according to another embodiment of the invention.

FIG. 12 is a perspective view of the proximal end 3A, the holder 4 and the external apparatus 27, according to another embodiment of the invention. In another characteristic of this embodiment, the invention is exchanged in the holder 4 with various types of external apparatus 27, with other surgical instruments and surgical devices. In another characteristic of this embodiment, the surgery may be initiated using an external apparatus 27 configured for manual use, the holder 4 is adapted to be disconnected from an external apparatus 27 and connected to another external apparatus 27 during the surgery. In another characteristic of this embodiment, the invention is adapted to be connected to the robotic arm 27D, subsequently disconnected of the robotic arm 27D and connected to another robotic arm 27D but is not limited to them.

Figure 13:
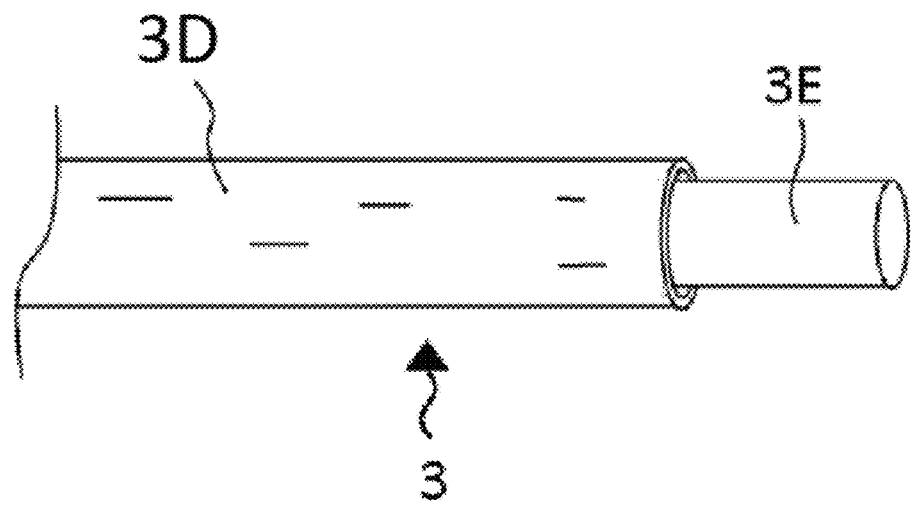
FIG. 13 is a perspective view of a portion of the elongated rod 3, according to another embodiment of the invention.

FIG. 13 is a perspective view of a portion of the elongated rod 3, according to another embodiment of the invention.

In other characteristic of this embodiment, the elongated rod 3 includes the support rod 3D and the nuclear rod 3E. In other characteristic of this embodiment, the elongated rod 3 is a tube, the nuclear rod 3E is located within the support rod 3D.

In other characteristic of some embodiments of the invention, the nuclear rod 3E has the same function of the command rod 3C. In one characteristics of this embodiment, the command rod 3C moves longitudinally in relation to the elongated support rod 3D. Also, the command rod 3C rotates with respect to elongated support rod 3D.

Figure 14:
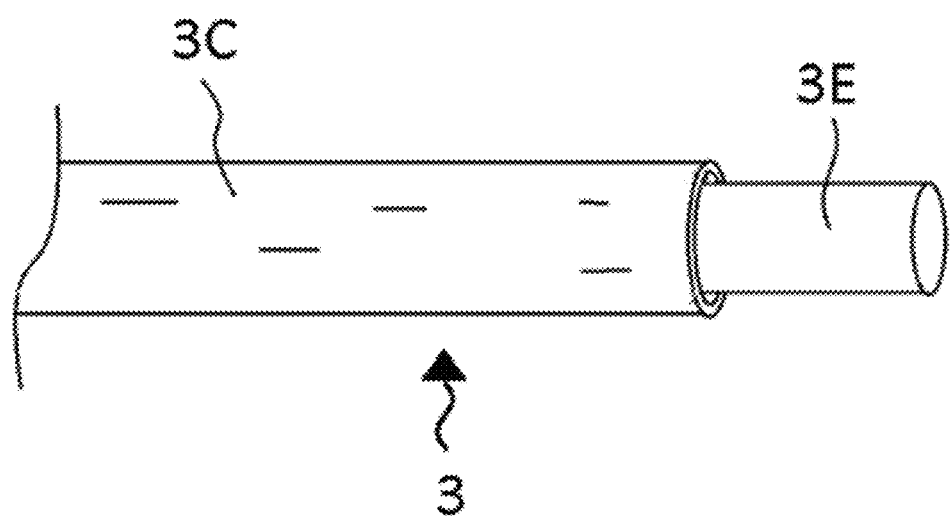
FIG. 14 is a perspective view of a portion of a command rod 3C, according to another embodiment of the invention.

FIG. 14 is a perspective view of a portion of the command rod 3C according to another embodiment of the invention.

In other characteristic of this embodiment, the elongated rod 3 includes the command rod 3C and the nuclear rod 3E. Other characteristic of this embodiment of the invention, the nuclear rod 3E is the support rod 3D, and the nuclear rod 3E has a support function. In another characteristic of this embodiment, the command rod 3C moves longitudinally in relation to the nuclear 3E elongated rod 3. In another characteristic of this embodiment, the command rod 3C moves longitudinally in relation to the nuclear rod 3E. Also, the command rod 3C rotates with respect to the nuclear rod 3E.

Figure 15:
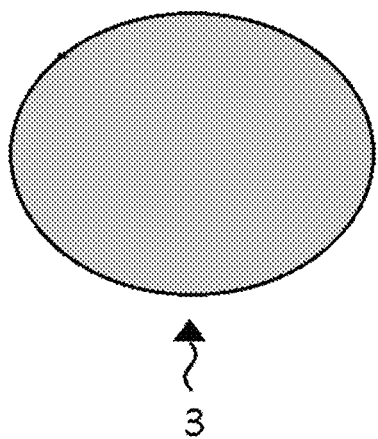
FIG. 15 is a cross sectional view of a portion of the elongated rod 3, according to another embodiment of the invention.

FIG. 15 is a cross sectional view of a portion of the elongated rod 3 according to another embodiment of the invention.

In another characteristic of this embodiment, the elongated rod 3 is solid. In other characteristic of this embodiment, the elongated rod 3 is solid and is adapted to be used as the command rod 3C or as the support rod 3D. In another characteristic of some embodiments, the elongated rods 3 are the command rods 3C. In another characteristic of some embodiments, the support rod 3D has a support function.

Figure 16:
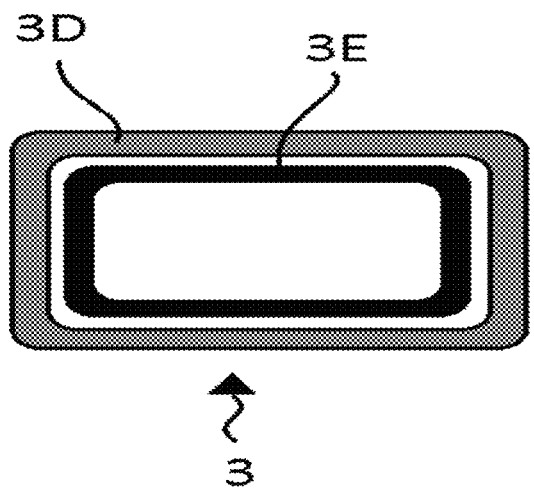
FIG. 16 is a cross-sectional view of a portion of the elongated rod 3 in a rectangular shape, in accordance with another embodiment of the invention.

FIG. 16 Is a cross-sectional view of a portion of the elongated rods 3 in a rectangular shape, in accordance with another embodiment of the invention.

In other characteristics of this embodiment, the support rod 3D is adapted to have the nuclear rod 3E within it. In another characteristic of this embodiment, the nuclear rod 3E is adapted to work as an interchangeable rod 3F. In another characteristic of this embodiment, the nuclear rod 3E is adapted to work as a command rod 3C or as a support rod 3D.

Figure 17:
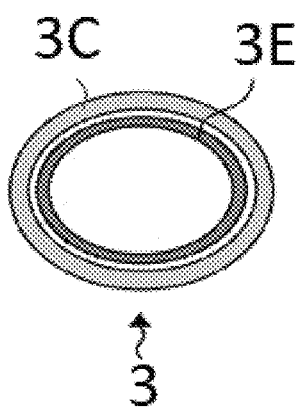
FIG. 17 is a cross-sectional view of a portion of the elongated rod 3 according to another embodiment of the invention.

FIG. 17 is a cross-sectional view of a portion of the elongated rod 3 according to another embodiment of the invention.

In another characteristic of this embodiment, the elongated rod 3 includes the command rod 3C and the nuclear rod 3E therein.

In one characteristic of some embodiments, the elongated rod 3 includes the cavity 9 with the nuclear rod 3E therein, and the elongated rod 3 is the support rod 3D, and the nuclear rod 3E is the command rod 3C. In other embodiments, the elongated rod 3 includes the cavity 9 with the nuclear rod 3E therein, and the elongated rod 3 is the command rod 3C and the nuclear rod 3E is the support rod 3D. In one characteristic of some embodiments, the nuclear rod 3E is a cable 16.

Figure 18:
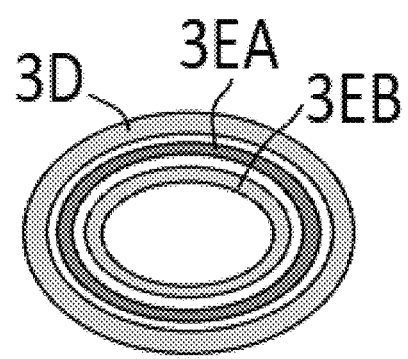
FIG. 18 is across sectional view of the elongated rod 3 according to another embodiment of the invention.

FIG. 18 is across sectional view of the elongated rod 3 according to another embodiment of the invention.

In another characteristic of this embodiment, the elongated rod 3 includes the support rod 3D and two nuclear rod 3E: a nuclear rod 3EA with other nuclear rod 3EB inside. In another characteristic of this embodiment, the nuclear rod 3EB is inside the nuclear rod 3EA. In another characteristic of some embodiment, each of the nuclear rod 3E are adapted to work as the command rod 3C. In another characteristic of some embodiment, each nuclear rod 3E is adapted to work as the support rod 3D. In another characteristic of some embodiments of the invention, there are a plurality of nuclear rod 3E. In some embodiments, at least one nuclear rod 3E is the support rod 3D. In another characteristic of some embodiments of the invention, at least one nuclear rod 3E is the command rod 3C. In one characteristic of some embodiments, the nuclear rod 3E includes the electric wire 52; in some embodiments the nuclear rod 3E includes a liquid for hydraulic action; in some embodiments the nuclear rod 3E includes an optical fiber; in some embodiments the nuclear rod 3E includes a wire; in some embodiments the nuclear rod 3E includes a gas but is not limited to them.

Figure 19:
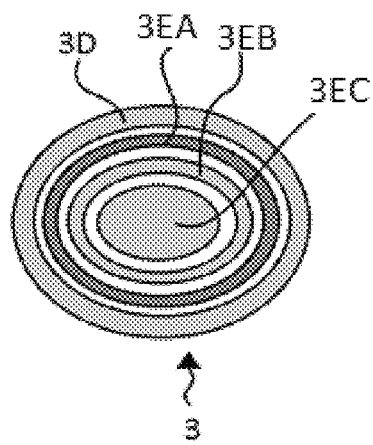
FIG. 19 is a cross sectional view of the elongated rod 3 according to another embodiment of the invention.

FIG. 19 is a cross sectional view of the elongated rod 3 according to another embodiment of the invention.

In one characteristic of this embodiment, the elongated rod 3 includes three nuclear rod 3E: the nuclear rod 3EA, the nuclear rod 3EB, and the nuclear rod 3EC in other characteristics of this embodiment, the three nuclear rod 3E are command rods 3C.

In another characteristic of this embodiment, the nuclear rod 3EC is inside the nuclear rods 3EB and the nuclear rod 3EB is inside the nuclear rod 3EA. In other characteristics of this embodiment, all the nuclear rod 3E operates independently. In one characteristic of some embodiments, each of the nuclear rod 3E are adapted to rotate relative around to the support rod 3D axis; in one characteristic of some embodiments, each of the nuclear rod 3E is adapted to slide lengthwise. In some embodiments, the nuclear rod 3E is the cable 16. In some embodiments, the nuclear rod 3E is a wire.

In other characteristics of some embodiments of the invention, the elongated rod 3 includes the support rod 3D and the command rod 3C. In some embodiments, the elongated rod 3 includes at least one support rod 3D. Another characteristic of some embodiments of the invention is that the elongated rod 3 includes at least one command rod 3C.

In other characteristics of some embodiments of the invention, the support rods 3D connects to the functional element 1 and to the holder 4 for support function.

In other characteristics of some embodiments of the invention, the command rod 3C connects the holder 4 to the functional element 1 for the transmission of, at least one of: force, power and torque to the functional element 1.

In other characteristics of some embodiments of the invention, the command rod 3C acts on the functional element 1 to make it perform its function. Another characteristic of some embodiments of the invention is that the support rods 3D fixes the functional element 1 to the holder 4.

Figure 20:
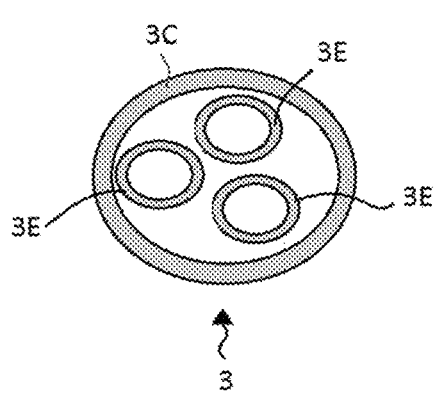
FIG. 20 is a cross sectional view of the elongated rod 3 according to another embodiment of the invention.

FIG. 20 is a cross sectional view of the elongated rod 3 according to another embodiment of the invention. In other characteristics of this embodiment, the elongated rod 3 includes three nuclear rod 3E that act independently of one another. In one characteristics of this embodiment, the elongated rod 3 is adapted to move along or rotate. In one characteristic of some embodiments, the nuclear rod 3E is the cable 16. In one characteristic of some embodiments, there are two nuclear rods 3E; in some embodiments there are three nuclear rod 3E, but the number of nuclear 3E is not limited to them.

Figure 21:
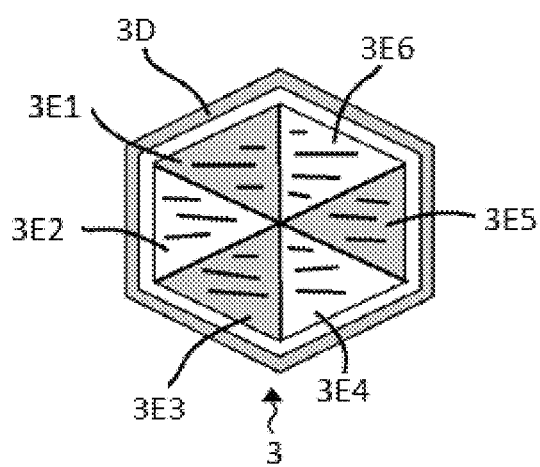
FIG. 21 is a cross sectional view of the elongated rod 3 according to another embodiment of the invention.

FIG. 21 is a cross sectional view of the elongated rod 3 according to another embodiment of the invention.

In other characteristics of this embodiment, the support rod 3D is hexagonal and includes six nuclear rods 3E in triangular format: nuclear rods 3E1, nuclear rods 3E2, nuclear rods 3E3, nuclear rods 3E4, nuclear rods 3E5, and nuclear rod 3E6. In one characteristic of some embodiments, each nuclear rod 3E is adapted to move longitudinally independently one of another. In other characteristic of this embodiment, the command rod 3C is adapted to be connected functionally on the functional element 1 in six different ways, with six nuclear rod 3E.

In one characteristic of some embodiments, the support rod 3D connects to the functional element 1 with a support function. In one characteristic of some embodiments, the support rod 3D supports the functional element 1 so the six nuclear rod 3E are adapted to act on six functional mechanisms of the functional element 1.

In one characteristic of some embodiments, the cross-section shape of the elongated rod 3 is round; in some embodiments, the cross-section shape of the elongated rod 3 is elliptical; in some embodiments, the cross-section shape of the elongated rod 3 is square. In one characteristic of some embodiments, the cross-section shape of the elongated rod 3 is rectangular; in some embodiments, the cross-section shape of the elongated rod 3 is hexagonal, but the cross-sectional shape of the elongated rod 3 is not limited to them. In one characteristic of some embodiments, at least one the elongated rod 3 is electrically insulating. In one characteristic of some embodiments, at least a portion of the elongated rods 3 are electrically insulating, for example: using it with the electric scalpel. In one characteristic of some embodiments, the elongated rod 3 is coated with a layer to facilitate the slippage, and to decrease friction. In one characteristic of some embodiments, the elongated rod 3 are coated with polytetrafluoroethylene.

Figure 22:
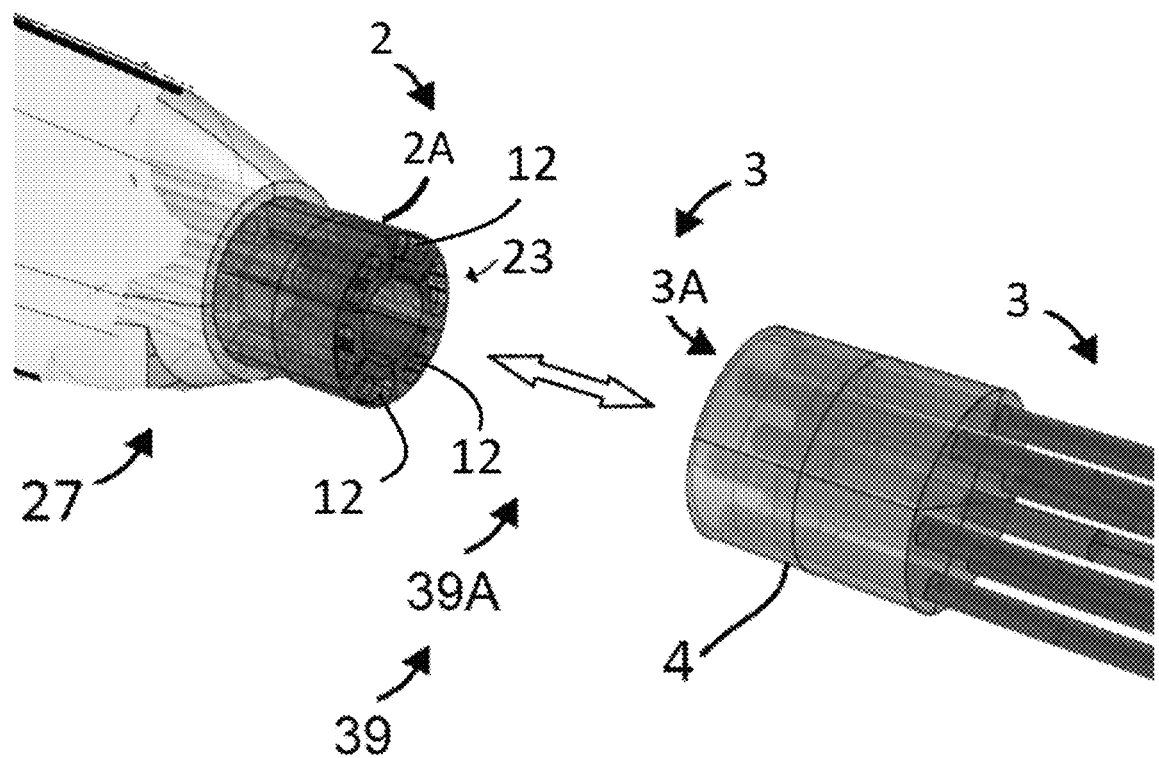
FIG. 22 is a perspective view of the invention showing a proximal quick connection system 39A, according to another embodiment of the invention.

FIG. 22 is a perspective view of the invention showing the quick connection system 39, according to another embodiment of the invention.

In other characteristics of this embodiment, the quick connection system 39 connects the holder 4 to the external apparatus 27 rapidly. In other characteristics of this embodiment, the holder 4 is connected in the external apparatus 27 in a quick form using the quick connection system 39A, which allows to connect the holder 4 and all the elongated rods 3 at a single time. In other characteristics of this embodiment, the command rod 3C connects to the external apparatus 27 in a functional way, and the support rod 3D are adapted to connect as support function.

In other characteristics of this embodiment, after connecting the command rods 3C to the external apparatus 27, the command rods 3C are adapted to receive and transmit to the functional element 1, force, power and torque provided by the external apparatus 27.

In one characteristic of some embodiment the invention includes de external apparatus 27. In one characteristic of some embodiment, the invention includes the external apparatus 27 and the external apparatus 27 is adapted to work with a plurality of functional elements 1. In one characteristic of some embodiments, the external apparatus 27 is the robotic arm 27D; in some embodiments the external apparatus 27 is the surgical robot 27H; in some embodiments the external apparatus 27 is the video camera 27C; in some embodiments the external apparatus 27 is the vacuum hose 271; in some embodiments, the external apparatus 27 is the laser device 27J; in some embodiments the external apparatus 27 is a device with servomotors 27K; in some embodiments the external apparatus 27 is the handle 27E; in some embodiment, the external apparatus 27 is the electric source 27L; in some embodiments the external apparatus 27 is the ultrasonic generator 35; in some embodiments the external apparatus 27 is the power source 27M, but not limited to them.

In other characteristics of this embodiment, the external apparatus 27 has the quick connection system 39A, and is adapted to be replaced quickly during surgery, for example: starting a surgery using a manual external apparatus 27, then switching to the robot arm 27D; or switching to a image processor 27A; or switching to the surgical stapler 58 manipulator 27G, but is not limited to them.

In other characteristics of this embodiment, the interchangeable rod 3F is adapted to be replaced during the surgical procedure, for example: using the tool 8 that is a scissors and changing it to an electric scalpel tool 8, remove the functional element 1, remove the command rod 3C and insert in the invention an electric scalpel that is the elongated rod 3 with insulation and the tool 8.

In other characteristics of some embodiments, at least one of said elongated rods 3 works as the tool 8 to perform a surgery. In other characteristics of this embodiment, some elongated rod 3 are the tool 8, for example, an electric scalpel command rod 3C is adapted to be introduced in the invention and used to perform surgery directly on the tissue 25, another example is the command rod 3C is adapted to be used as an ultrasonic scalpel. In other characteristics of this embodiment, the command rod 3C acts on its own tool 8.

In another characteristic of this embodiment, the interchangeable rod 3F is adapted to work as an electrical scalpel. In other characteristics of this embodiment, the interchangeable rod 3F is adapted to work as a needle; the interchangeable rod 3F is adapted to work as a heat transmitter; the interchangeable rod 3F is adapted to work as a cold transmitter; the interchangeable rod 3F is adapted to work as a tube; the interchangeable rod 3F is adapted to work as ultrasonic scissors but is not limited to them.

In other characteristics of this embodiment, the interchangeable rod 3F is provided with an outer sheathing insulating layer for use with an electric scalpel. In another characteristic of this embodiment, the interchangeable rod 3F is adapted to work as an electric scalpel. In other characteristics of this embodiment, the interchangeable rod 3F is adapted to work with an ultrasonic scissors. In other characteristic of this embodiment, the interchangeable rod 3F is adapted to work as a tube. In other characteristics of this embodiment, the interchangeable rod 3F include a LED 51 or fiber optic lighting but is not limited to them.

Figure 23:
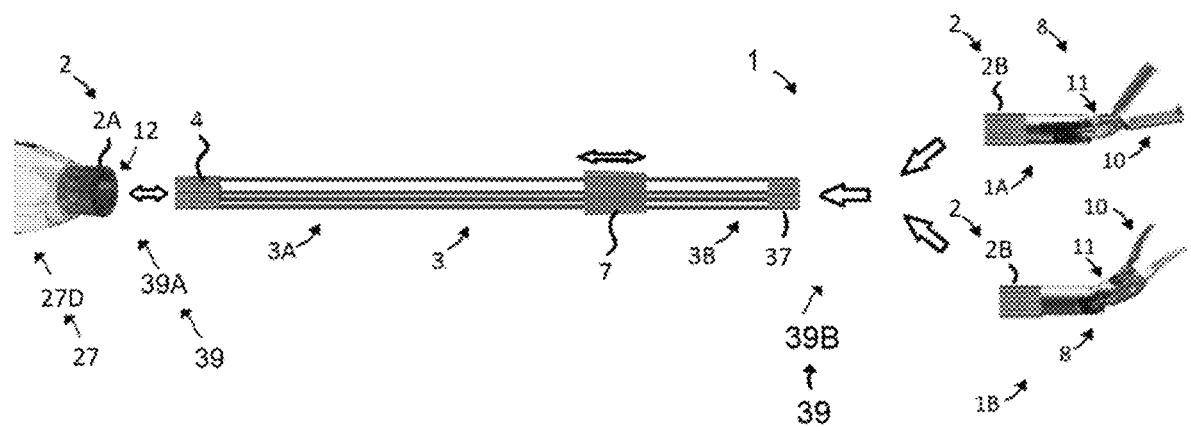
FIG. 23 is a perspective view of another embodiment of the invention configured to connect to a robotic arm 27D.

FIG. 23 is a perspective view of another embodiment of the invention configured to connect to the robotic arm 27D. In one characteristic of some embodiments, the invention is part of the robotic arm 27D. In this example, the holder 4 is disconnected from the robotic arm 27D. In other characteristics of this embodiment, it has four elongated rod 3, three of them being the support rods 3D and one being the command rod 3C. In other characteristics of this embodiment, the protector guide 7 is adapted to run on the elongated rod 3 of the proximal end 3A to the distal end 3B, as indicated by the two-headed arrow.

In other characteristics of this embodiment, two functional elements 1 are available to connect to the distal end 3B, the functional element 1A and the functional element 1B. In other characteristics of this embodiment, the functional element 1 is adapted to be used and replaced by another during surgery, the type of functional element 1 that will be used is not limited to them. In another characteristic of this embodiment, the tool 8 that will be used is not limited to them. In another characteristic of this embodiment, the functional element 1 includes the tool 8, the connector 37 and the adapter 2B.

Figure 24:
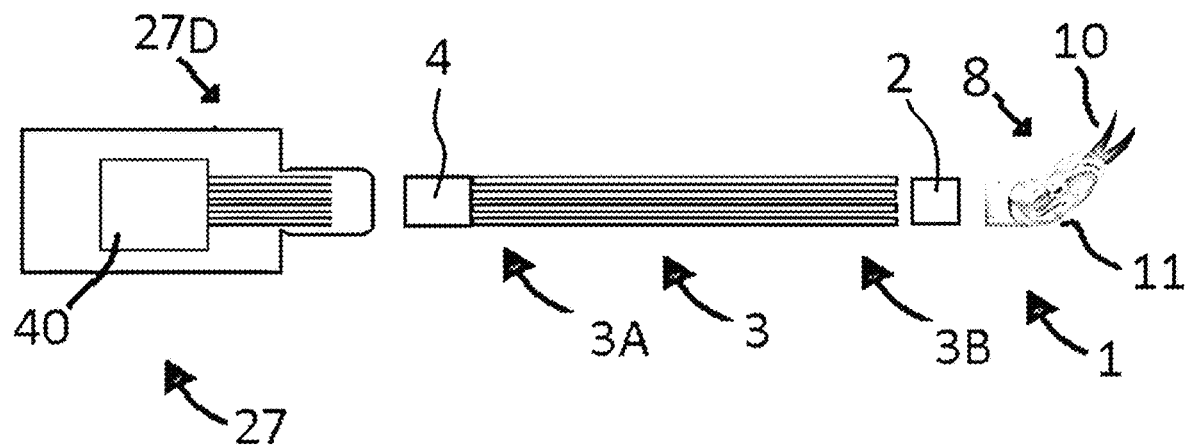
FIG. 24 is a side lateral cross-sectional view of the invention adapted to be robotic operating, according to another embodiment of the invention.

FIG. 24 is a lateral cross-sectional view of another embodiment of the invention adapted to be robotic operating. In another characteristic, this embodiment is adapted to work with the external apparatus 27, according to another embodiment of the invention.

In another characteristic of this embodiment, the external apparatus 27 is the robotic arm 27D. In other characteristics of this embodiment, the holder 4 is configured to detachably connect to the robotic arm 27D to perform a robotic surgery. In other characteristics of this embodiment, the robotic arm 27D has servo motors 40 to actuate in the command rod 3C. In one characteristic of some embodiments, the number of the servo motors 40 in the robotic arm 27D is not limited to one.

In another characteristic of this embodiment, the robotic arm 27D is detachably connected to the holder 4 by the quick connection system 39.

In another characteristic of this embodiment, the quick connection system 39A connects each of the command rod 3C to the servo motors 40 of the robotic arm 27D. In another characteristic of this embodiment, the robotic arm 27D is adapted to transmit, at least one of, force, power and torque to, at least one of, the command rod 3C.

In another characteristic of this embodiment, the robotic arm 27D moves the command rod 3C to manipulate the functional element 1.

In another characteristic of this embodiment, the robotic arm 27D is adapted to use the command rods 3C.

In another characteristic of this embodiment, it is adapted to interchangeably connect to a plurality of functional elements 1. In another characteristic of this embodiment, the elongated rods 3 controls the functional element 1. In another characteristic of this embodiment, the functional element 1 is modular. In another characteristic of this embodiment, one part the functional element 1 is movable with respect to one another in a first plane and said parts are pivotable relative to said distal end 3B of said shaft in said first plane. In another characteristic of this embodiment, the tool 8 is movable with respect to the adapter 2 in a first plane and are pivotable relative do the distal end 3B in a second plane.

Figure 25:
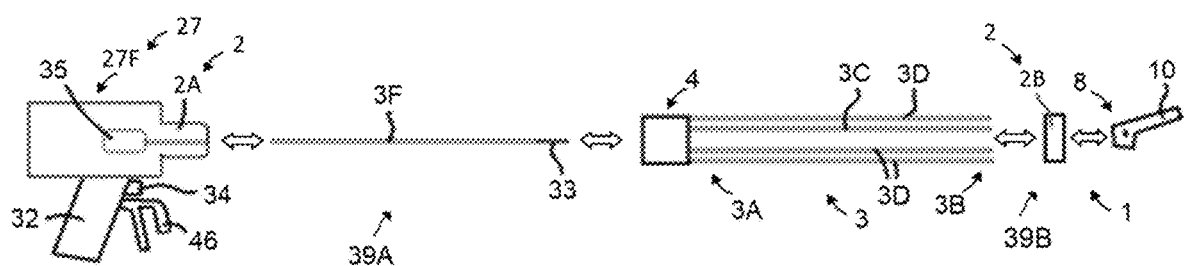
FIG. 25 is the lateral view of another embodiment of the invention, including an ultrasonic device 27F.

FIG. 25 is the lateral view of another embodiment of the invention, including the ultrasonic device 27F, according to another embodiment of the invention.

In this embodiment, the functional element 1 is modular, including the adapter 2, and the tool 8 including one jaw 10A.

In one characteristics of this embodiment, the functional element 1 is connectable from the distal end 3B. In one characteristics of this embodiment, the holder 4 is connectable from de external apparatus 27. In one characteristics of this embodiment, the interchangeable rod 3F is connectable from the holder 4.

In one characteristics of this embodiment, the holder 4 is adapted to connect to the interchangeable rod 3F, the interchangeable rod 3F is adapted to be inserted in the holder 4. In one characteristics of this embodiment, the tool 8 is adapted to connect to the adapter 2B and the functional element 1 is adapted to connected to the distal end 3B.

In another characteristic of this embodiment, the functional element 1 connects disconnectedly to the distal end 3B.

Another characteristic of this embodiment is that the interchangeable rod 3F is adapted to be disconnected from the holder 4 and replaced by other interchangeable rod 3F during a surgery.

One characteristic of this embodiment is the longitudinal movement of a trigger 46, which drives the command rod 3C in a longitudinal move that drives the jaws 10A to open and close relative to a blade 33 to cut.

In one characteristic of some embodiments of the ultrasonic device 27F, the ultrasonic generator 35 is located in the external apparatus 27. In one characteristic of some embodiments, the ultrasonic generator 35 is located in the functional element 1.

In other characteristics of this embodiment, the battery 32 is in the external apparatus 27. In one characteristic of some embodiments, the command rod 3C conducts electrical energy to the ultrasonic generator 35 in the functional element 1. In another characteristic of this embodiment, the elongated rod 3 is an electric conductor that has an insulating outer layer. Another characteristic of this embodiment, the ultrasonic generator transmits power, force and torque to the command rod 3C in order to make the blade 33 the cutting member. In another characteristic of this embodiment, the functional element 1 is adapted to pass through a conventional trocar 49.

Figure 26:
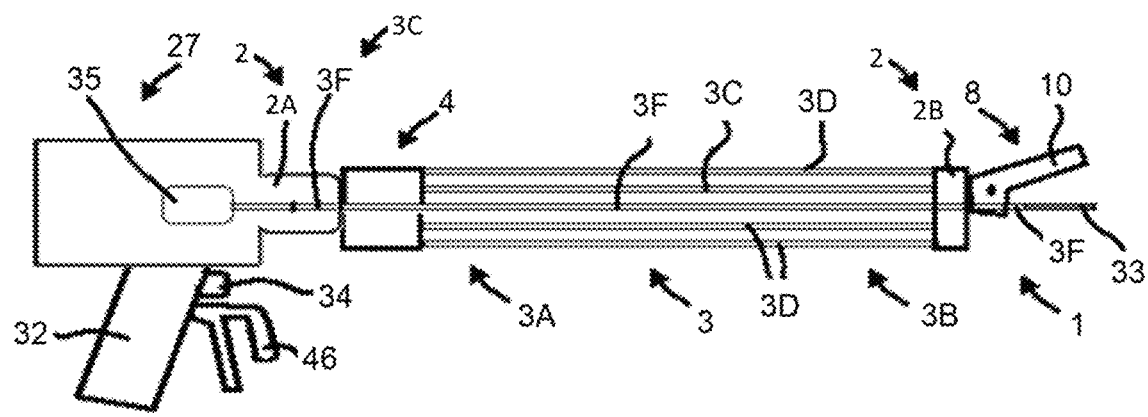
FIG. 26 is a cross-sectional view of another embodiment of the invention, including the ultrasonic device 27F.

FIG. 26 is a cross-sectional view of another embodiment of the invention, including the ultrasonic device 27F. One characteristics of this embodiment, the jaws 10A are connected to the adapter 2. One characteristics of this embodiment, the interchangeable rod 3F is connected and ready for use. In one characteristics of these embodiments, a button 34 activates the ultrasonic generator 35 which acts on the interchangeable rod 3F making the ultrasonic device 27F functional.

Other characteristics of this embodiment, moving forward, the trigger 46 causes the command rod 3C to move the jaws 10A towards the blade 33. Other characteristics of this embodiment, the pressing the button 34 drives the ultrasonic generator 35, which uses the energy of the batteries 32 to move the blade 33 to cut.

Figure 27:
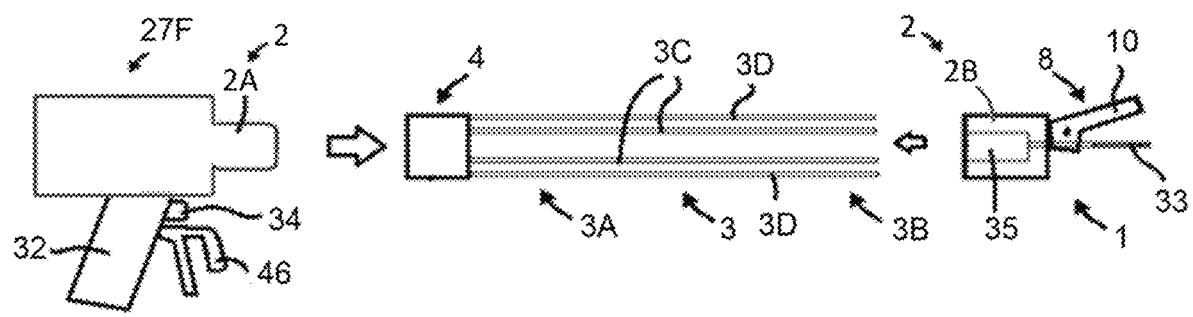
FIG. 27 is the lateral view of another embodiment of the invention including an ultrasonic device 27F and an ultrasonic generator 35 located in the functional element 1.

FIG. 27 is the lateral view of another embodiment of the invention including the ultrasonic device 27F. In one characteristics of this embodiment, the holder 4 is connectable to the external device 27. In another characteristic of this embodiment, the external device 27 is the ultrasonic device 27F.

Another characteristic of this embodiment is that the interchangeable rod 3F is adapted to be disconnected from the holder 4 and replaced by other interchangeable rod 3F during surgery, In one characteristics of this embodiment, the functional element 1 is a single piece and connectable to the distal end 3B, the larger arrow shows the direction in which the external device27F connects to the holder 4. The minor arrow shows the direction in which the functional element 1 connects to the distal end 3B.

Another characteristic of this embodiment is the longitudinal movement of the trigger 46 drives the command rod 3C causing the jaws 10A to open and close relative to the blade 33 to cut.

In other characteristics of this embodiment, in the command rod 3C exists electric wires connecting the battery 32 to the ultrasonic generator 35. In another characteristic of this embodiment, the ultrasonic generator 35 is located in the functional element 1. In one characteristic of some embodiments, the battery 32 may be used as the handler. In another characteristic of this embodiment, which actuating the button 34 the ultrasonic generator 35 that drives the blade 33 to cut. In another characteristic of this embodiment, the functional element 1 is adapted to pass through the conventional trocar 49. In another characteristic of this embodiment, the functional element 1 connects disconnectedly to the distal end 3B. In another characteristic of some embodiments, the functional element 1 is modular. In one characteristic of some embodiments, the functional element 1 is a single piece.

Figure 28:
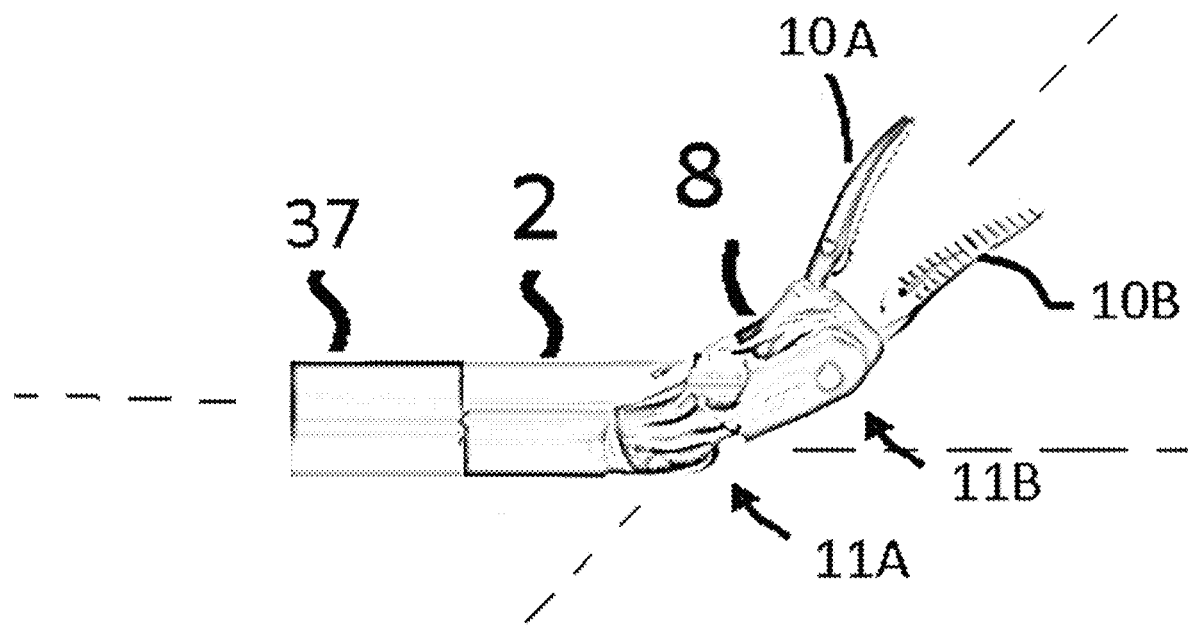
FIG. 28 and FIG. 29 are perspective views of other embodiments of the invention, in which the functional element 1 is articulable rotating, opening and closing on its jaws 10A and jaws 10B.
Figure 29:
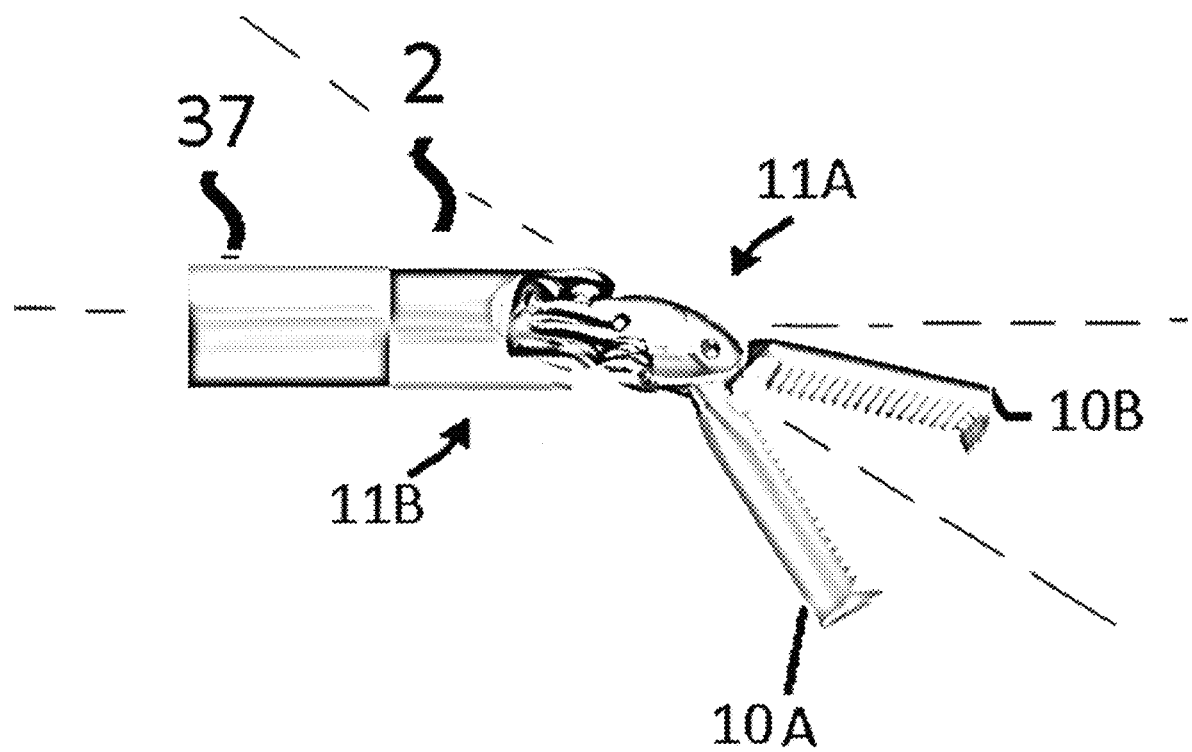

FIG. 28 and FIG. 29 are perspective views of other embodiments of the invention, in which the functional element 1 is articulable rotating, opening and closing its jaws 10A and jaws 10B. In one characteristics of this embodiment, the movement is carried out by means of rotors connected to the elongated rod 3, which connect to the functional element 1 to receive the commands of torque and power of the command rod 3C. In one characteristics of this embodiment, the functional element 1 is controlled from the external apparatus 27. In one characteristics of this embodiment, the tool 8, may be scissors and tweezers, but is not limited to them. In one characteristics of this embodiment, the functional element 1 comprises a pair of cooperating jaws 10A and 10B made to perform a surgical operation.

In one characteristics of this embodiment, the functional element 1 comprises two modular parts. In one characteristics of this embodiment, the functional element 1 is adapted to be robotic operating. In one characteristics of this embodiment, it comprises two articulations joint 11A and joint 11 B. In one characteristics of this embodiment, the functional element 1 is rotatable around two linear axes, around the axis of the instrument and around the axis of the tool 8. In one characteristics of some embodiments, the functional element 1 includes two movable parts with respect to one another in a first plane, and the parts are pivotable relative to said distal end 3B of said shaft in said first plane. In one characteristics of this embodiment, the functional element 1 is modular and detachably connected to said distal end 3B.

In one characteristics of this embodiment, the distal end 3B is adapted to interchangeably connect to a plurality of the functional elements 1.

Figure 30:
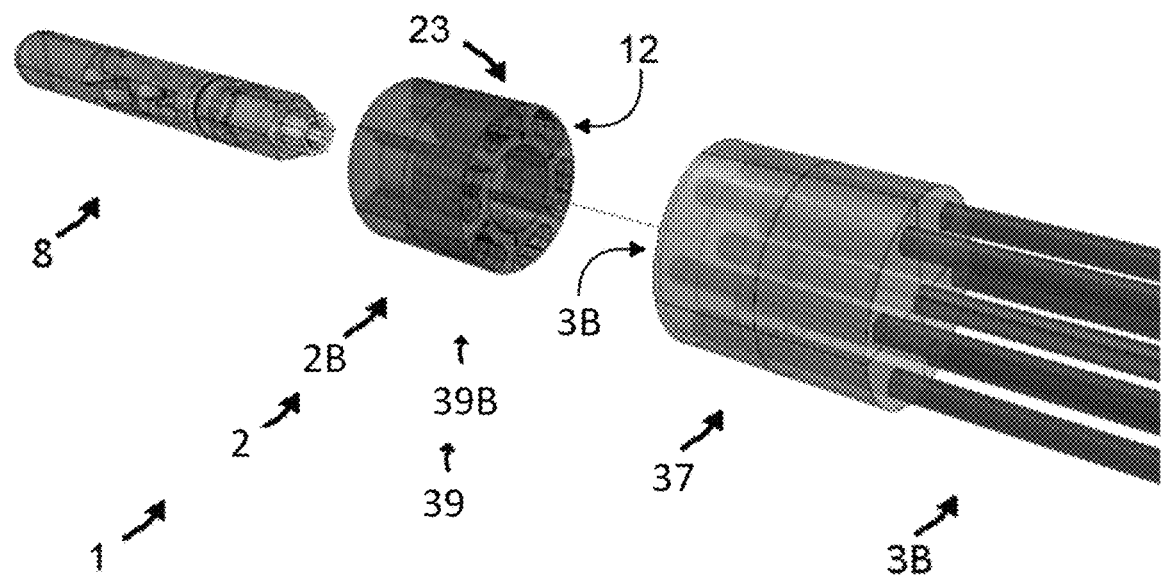
FIG. 30 is a perspective view of a tool 8, an adapter 2 and a connector 37 and the distal end 3B, according to another embodiment of the invention.

FIG. 30 is a perspective view of the tool 8, the adapter 2 and the connector 37 and the distal end 3B, according to another embodiment of the invention.

This functional element 1 include the quick connection system 39B, it is adapted to be quickly replaced by the adapter 2, the allowing the connection of several different types of tools 8. In one characteristics of this embodiment, the tool 8 is adapted to be quickly coupled and disconnected from the adapter 2. In one characteristics of this embodiment, the adaptor 2 is adapted to be quickly replaced with another adapter 2, is adapted to be quickly removed from the connector 37 and replaced with another adapter 2.

In some embodiments, the functional element 1 need to use several commands rods 3C, for example: the tool 8 that is a stapler 54 or the tool 8 that is an instrument for robotic surgery.

In some embodiments, the functional element 1 needs only one command rod 3D. In other characteristics of this embodiment, the same command rod 3C opens and closes the pair of jaws 10 with the longitudinal move and rotate the functional element 1 around one axis.

In some embodiments the functional element 1 needs to rotate around two or more axis, in this case the functional element 1 needs to use more than one commands rods 3C.

In one characteristics of this embodiment, the connector 37 facilitates the fitting of the adapter 2 in the distal end 3B of the elongated rod 3. In this example, to connect the adapter 2 in the connector 37, the adapter 2 is engaged in the connector 37 and rotated around its axis. To disconnect the adapter 2 from the connector 37, the adapter 2 is rotated around the reverse direction so as to disconnect the adapter 2 from the connector 37.

Figure 31:
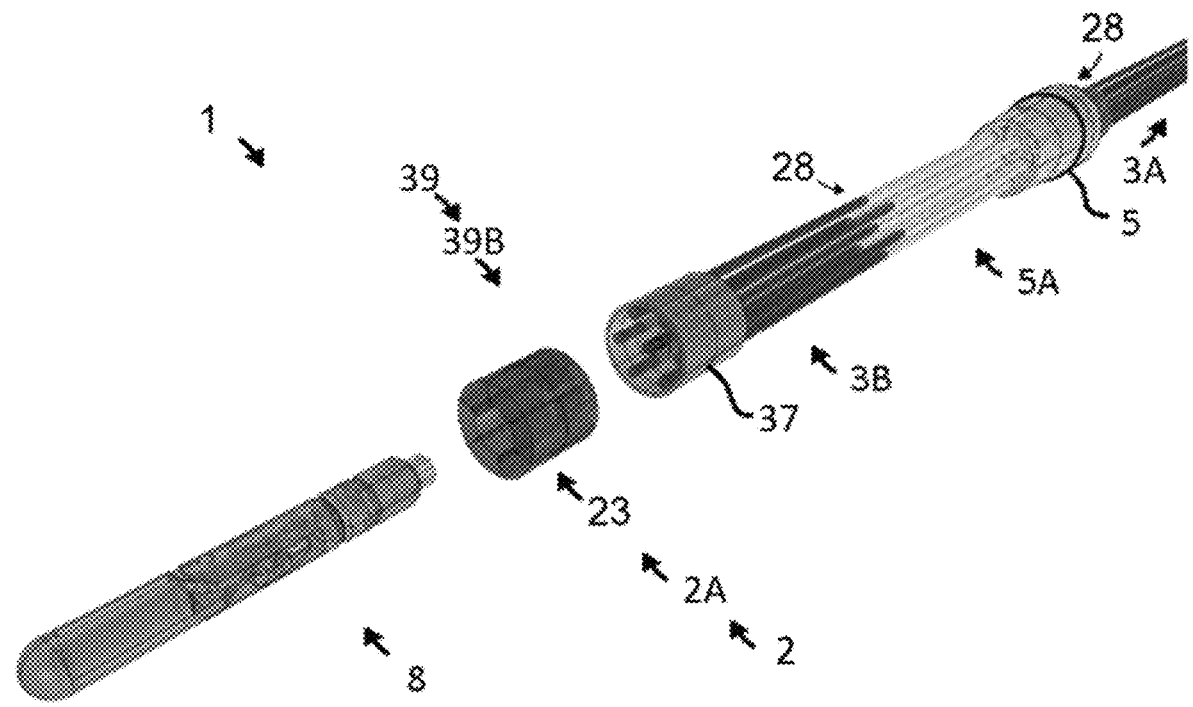
FIG. 31 is a perspective view of another embodiment of the invention, the functional element 1, including, the tool 8, the adapter 2 and the connector 37, and seven elongated rods 3 which are sectioned.

FIG. 31 is a perspective view of another embodiment of the invention, including the functional element 1, having, the tool 8, the adapter 2, and the connector 37; and seven elongate rods 3 which are sectioned to be viewed as the distal end 3B thereof. In one characteristics of this embodiment, the tool 8 is connectable from the adapter 2. In one characteristics of this embodiment, the connector 37 is connectable to the distal end 3B. In one characteristics of this embodiment, the distal elongated rod 3B has seven elongated rod 3.

In one characteristics of this embodiment, the connector 37 is adapted to engage the adapter 2. In that example, to connect the adapter 2 to the connector 37, the adapter 2 is engaged in the connector 37 and rotated. To disconnect the adapter 2 from the connector 37, the adapter 2 is rotated in the reverse direction in order to disconnect the adapter 2 from the connector 37.

In one characteristics of this embodiment, the free scar trocar 5 are used to transfix the tissue 25. In one characteristics of this embodiment, the cannulas 5A are adapted to cause minimum trauma to the tissue 25 in order to prevent scar. In one characteristics of this embodiment, the cannulas 5A have an outer diameter thin enough to cause minimal trauma to the tissue 25.

In one characteristics of this embodiment, the elongated rods 3 uses the lumens28 provided by the free scar trocar 5 to access the surgical site 26.

In one characteristics of this embodiment, the connector 37 is connected to the distal end 3B, inside the surgical site 26, after the elongate rods 3 pass through the free scar trocar 5.

Figure 32:
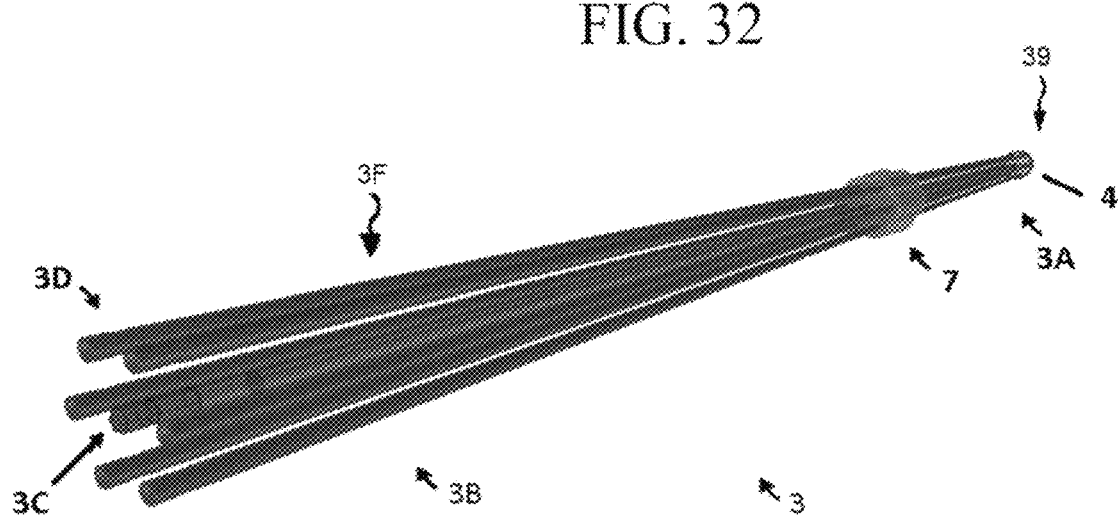
FIG. 32 and FIG. 33 are perspective views of the distal end 3B and the protector guide 7, according to another embodiment of the invention.
Figure 33:
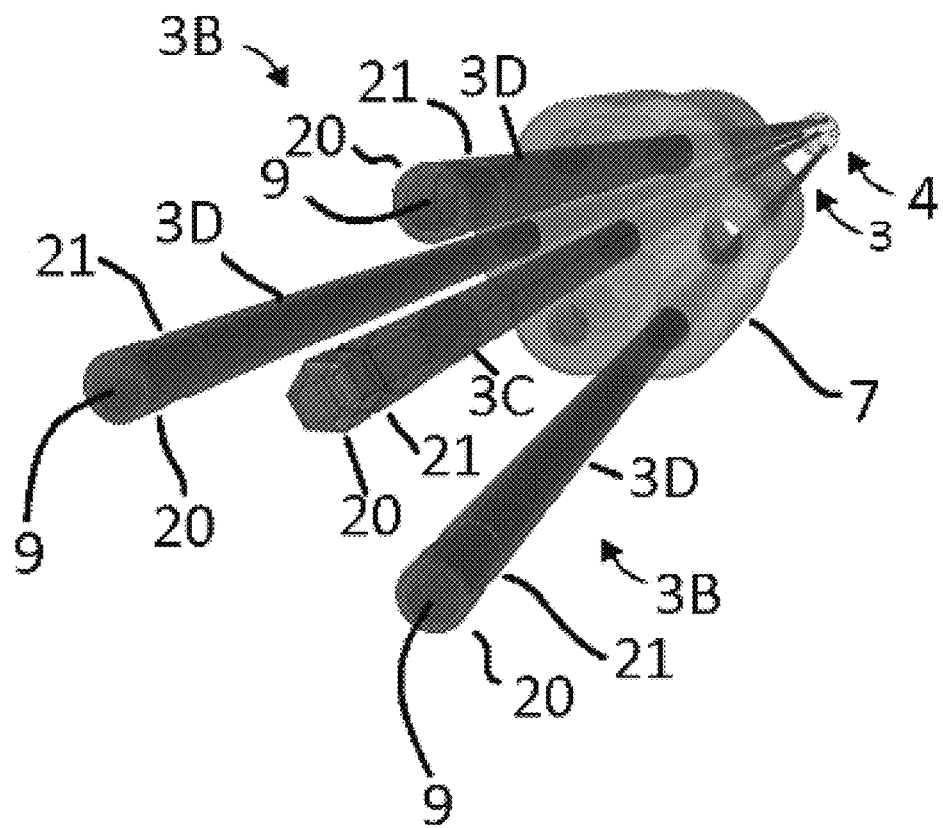

FIG. 32 and FIG. 33 are perspective view of the distal end 3B and the protector guide 7 according to another embodiment of the invention.

In one characteristics of this embodiment, the protector guide 7 is movable longitudinally with respect to the elongated rod 3. In another characteristic of this embodiments, the support rods 3D is the interchangeable rods 3F. In FIG. 32 there are seven elongated rods 3 and three interchangeable rods 3F. In FIG. 33 three interchangeable rods 3F were removed remaining four elongated rod 3 for use, three support rods 3D for support and one command rod 3C to provide strength, power and torque to the functional element 1. In one characteristics of this embodiment, the protector guide 7 protect the rods from inadvertently hurting something. In one characteristics of this embodiment, the protector guide 7 drive de replacement of the interchangeable rod 3F. In one characteristics of this embodiment, the protector guide 7 is usually fitted into a slot of the free scar trocar 5, so the elongated rod 3 are inserted into the free scar trocar 5 guided by the protector guide 7. In one characteristics of this embodiment, the elongated rod 3 have a slightly smaller diameter than the lumens28 of the cannulas 5A, so as to be able to move longitudinally inside the cannulas 5A. In some embodiments there are two protector guide 7. In one characteristics of this embodiment, the second protector guide 7B facilitates the removal of the interchangeable rod 3F and the replacement of the interchangeable rod 3F.

Figure 34:
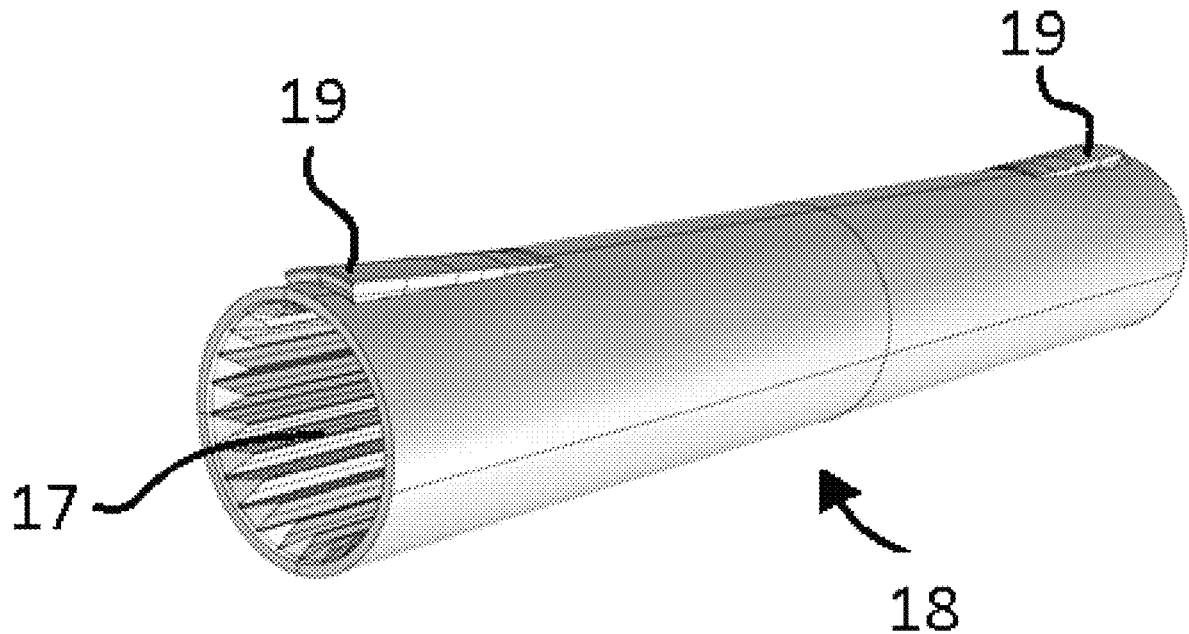
FIG. 34 and FIG. 35 are perspectives views of a link 18 according to another embodiment of the invention. In one characteristics of this embodiment, the link 18 allows to quickly connect two elongated rods 3.
Figure 35:
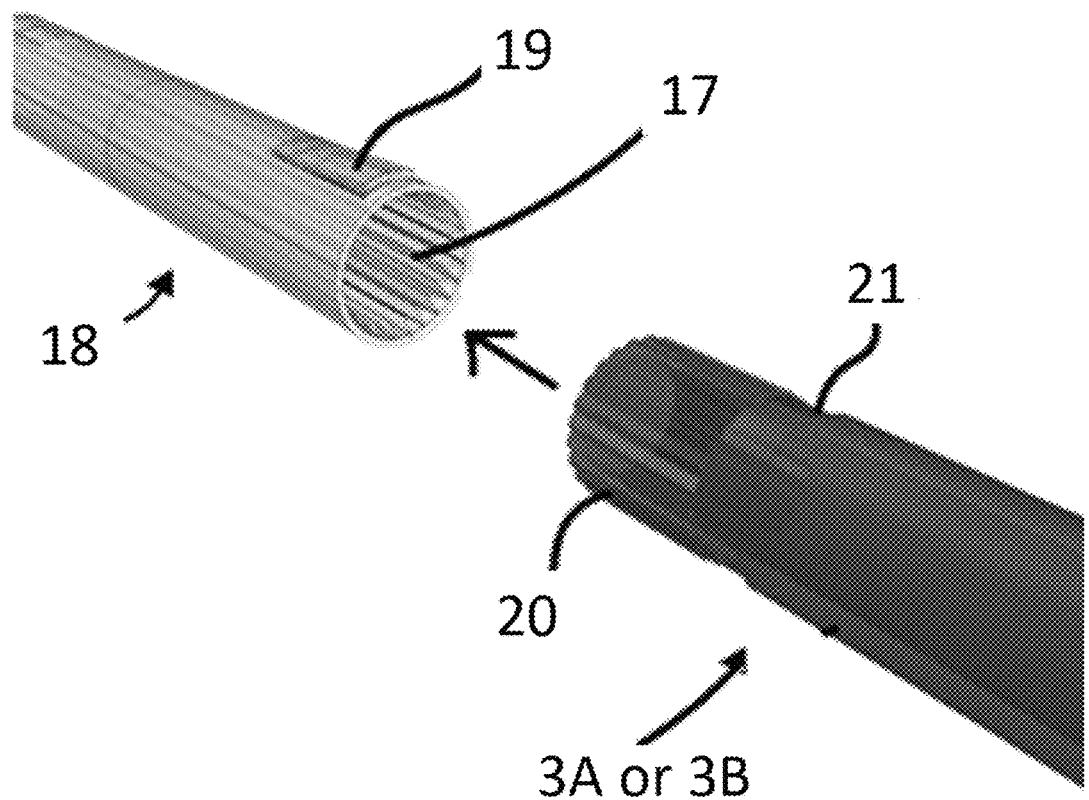

FIG. 34 and FIG. 35 are perspective views of the link 18 according to another embodiment of the invention, the quick connection system 39. In this embodiment, the distal end 3B has a gear 20 that engages the socket 17 to transmit torque. In one characteristics of this embodiment, the link 18 allows to quickly connect two elongated rods 3. In one characteristics of this embodiment, the distal end 3B enters and snaps into a socket 17. In one characteristics of this embodiment, a lock 19 of the link 18 prevents the elongate rod 3 from leaving. In one characteristics of this embodiment, the link 18 stays inside the housing 12. To connect the rod 3, the link 18 is pulled out of a housing 12 until the lock 19 rises. In one characteristics of this embodiment, the elongated rod 3 is docked and is pushed back to the housing 12 the lock 19 and the elongated rod 3 is connected. The elongated rod 3 moves inside a socket 17 to transmit torque and power force. In one characteristics of this embodiment, the link 18 is where the elongated rod 3 connects. In one characteristics of this embodiment, the link 18 allows the proximal end 3A and the distal end 3B to be connectable to the adapter 2A or adapter 2B. In one characteristics of this embodiment, the link 18 also connects the distal end 3B with the functional element 1. In one characteristics of this embodiment, the lock 19 engages a slit 21 to disconnectedly connect the elongated rod 3 to the link 18. In one characteristics of this embodiment, the arrow shows the direction in which the elongated rod 3 engages the socket 17.

Figure 36:
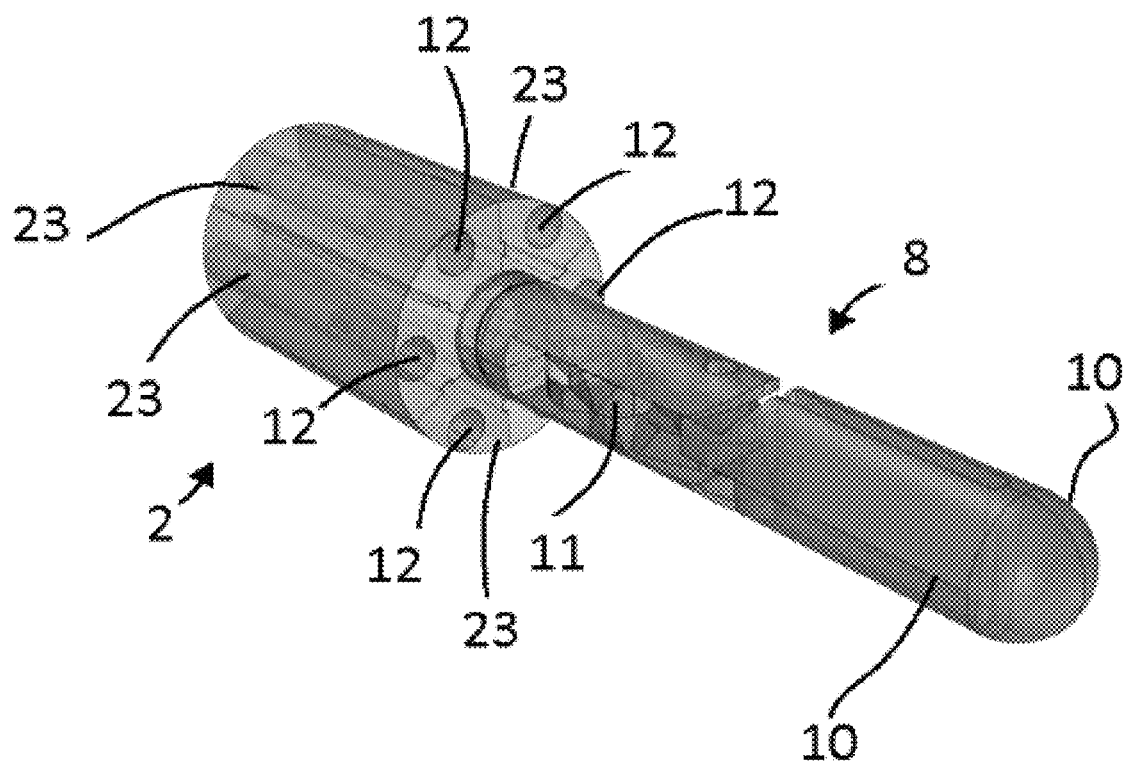
FIG. 36 is a perspective view of an embodiment of the functional element 1, according to another embodiment of the invention.

FIG. 36 is a perspective view of an embodiment of the functional element 1, according to another embodiment of the invention.

Various types of tools 8 are adapted to be inserted in the adapter 2. In one characteristics of this embodiment, the support rod 3D is adapted to connect in the housing 12 of the cart 23. In one characteristics of this embodiment, the control rod 3C is connectable to the tool 8. In the tool 8 there is a groove 24 which allows the tool 8 to rotate relative to its axis. In one characteristics of this embodiment, the articulation joint 11 is actionable by command rod 3C to open and close the pair of jaws 10. In one characteristics of this embodiment, the housing 12 is also used to connect other types of tools 8 to adapter 2. In one characteristics of this embodiment, the adapter 2 is adapted to be connect several types of tools 8. In one characteristics of this embodiment, the tool 8 is connected to the adapter 2A so that it is adapted to rotate around the adapter 2A axis. In one characteristics of this embodiment, the adapter 2A is adapted to be docked to the distal end 3B with the aid of the connector 37.

Figure 37:
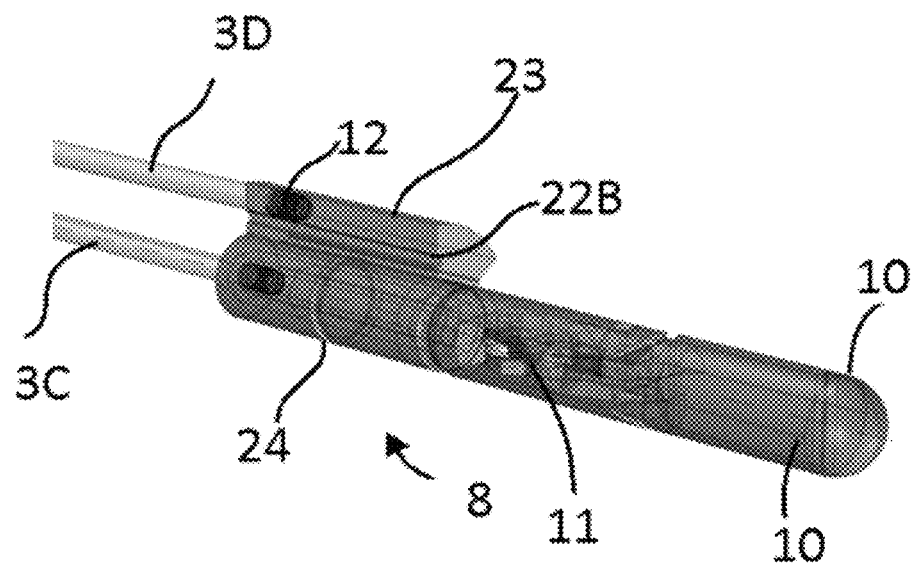
FIG. 37 is a perspective view of a portion of the functional element 1 directly connected to the distal end 3B, according to another embodiment of the invention.

FIG. 37 This is a perspective view of a portion of the functional element 1 directly connected to the distal end 3B, according to another embodiment of the invention.

Only one cart 23 is seen, the other carts 23 are removed for easy viewing. In one characteristics of this embodiment, the cart 23 is connected to the support rod 3D. In one characteristics of this embodiment, the command rod 3C is adapted to move longitudinally in the manner to drive the articulation joint 11. In one characteristics of this embodiment, the grove 24 allows the tool 8 to rotate without moving in the longitudinal direction. This allows the articulation joint 11 to be fired in order to open and close the jaws 10. A female rail 22B is seen.

Figure 38:
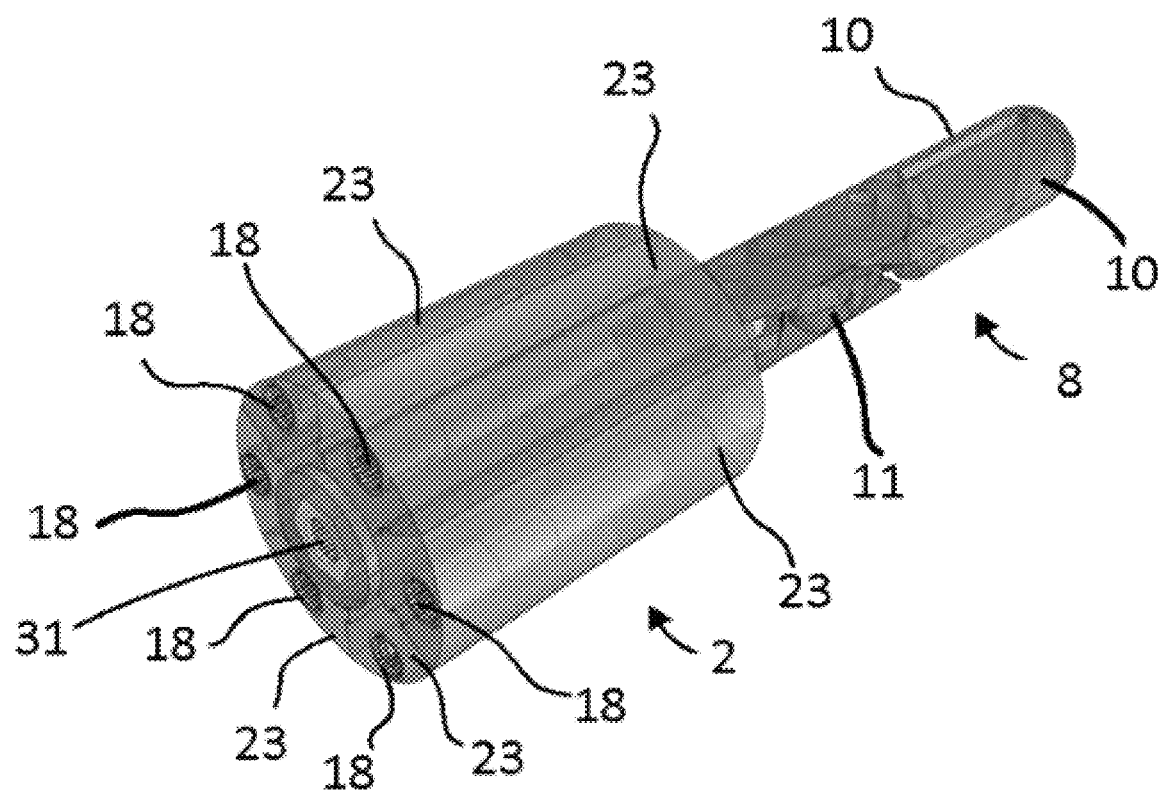
FIG. 38 is another embodiment of the invention that uses the link 18.

FIG. 38 This is another embodiment of the invention that uses the link 18 to connect the elongated rod 3 to the adapter 2. In one characteristics of this embodiment, a female connecter 31 connects the command rod 3C that opens and closes the pair of jaws 10 and rotates the tool 8. In other characteristic this embodiment, the cart 23 is adapted to work as a support function or as a control function. In one characteristics of this embodiment, the link 18 is adapted to transmit power, force a torque to the tool 8. In one characteristics of this embodiment, the cart 23 is adapted to be made of an electrical insulator material to connect to the elongated rod 3 that has a layer of insulation. In other characteristic this embodiment, cart 23 is adapted to be in electrical connection with the functional element 1. In other characteristics of this embodiment, at least one of said elongated rods 3 is adapted to be in electrical connection with the functional element 1.

Figure 39:
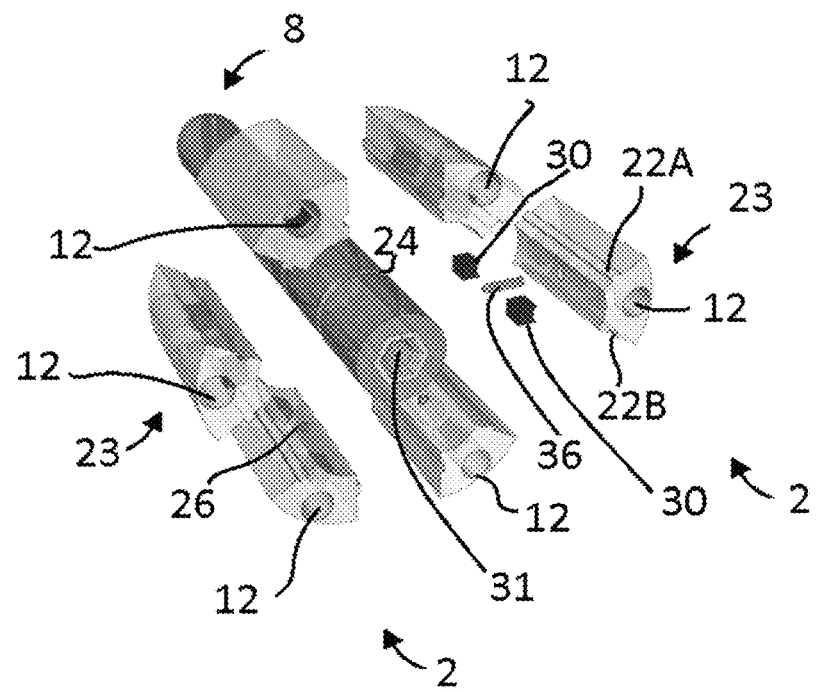
FIG. 39 is an exploded perspective view of the functional element 1, according to another embodiment of the invention.

FIG. 39 is an exploded perspective view of the functional element 1, according to another embodiment of the invention.

In one characteristics of this embodiment, a pin 36 engages the groove 24 and prevents the tool 8 from moving longitudinally while allowing it to rotate around its axis. In one characteristics of this embodiment, the female-connector 31 is where the command rod 3C connect to open and close the pair of jaws 10. In one characteristics of this embodiment, a beater 30 keeps the link 18 in the housings 12.

In one characteristics of this embodiment, a male rail 22A and the female rail 22B allow longitudinal displacement of the carts 23 and at the same time keeps one cart 23 connected to the other cart 23.

Figure 40:
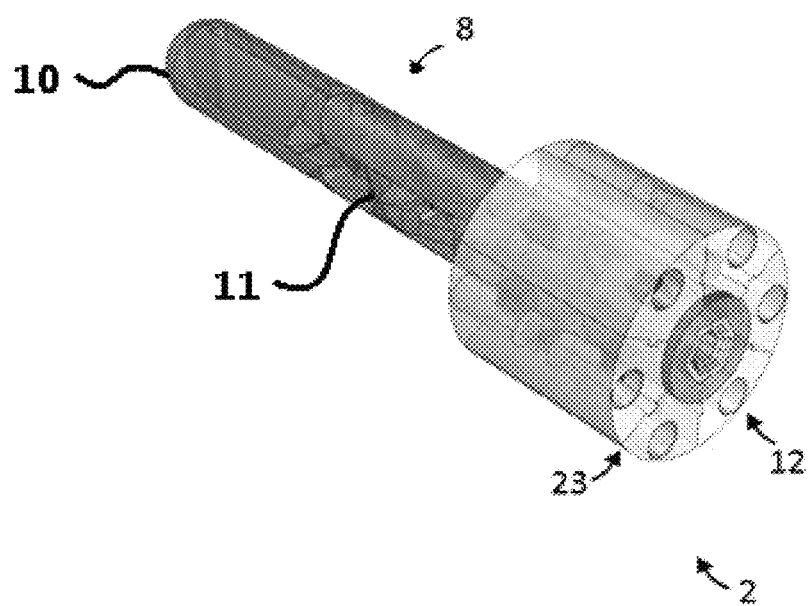
FIG. 40 is another view of a tool 8 connected to the adapter 2, according to another embodiment of the invention.

FIG. 40 is another view of the tool 8 connected to the adapter 2, according to another embodiment of the invention.

It is adapted to be connected directly to a distal end 3B or to the connector 37.

Figure 41:
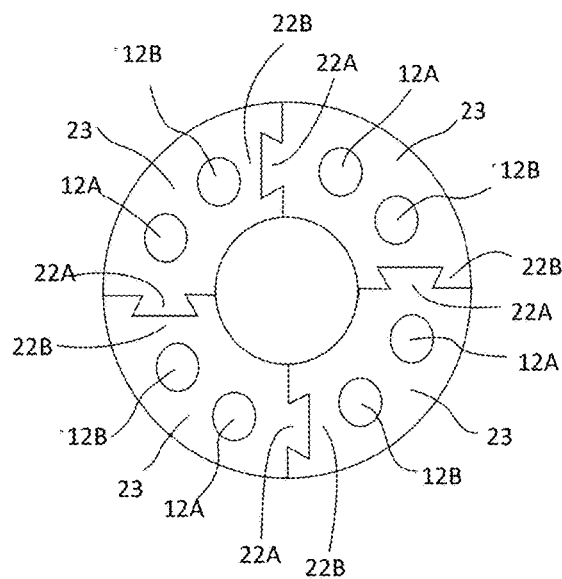
FIG. 41 is a trans sectional view of the adapter 2, with four carts 23, according to another embodiment of the invention.

FIG. 41 It is a trans sectional view of the adapter 2 with four cart 23, according to another embodiment of the invention.

In one characteristics of some embodiment, the number of carts 23 is not limited to these. In other characteristic this embodiment, each cart 23 has a housing 12A and another housing 12B. In one characteristics of this embodiment, the carts 23 have the male rails 22A and the female rails 22B, one slides longitudinally over the other.

Figure 42:
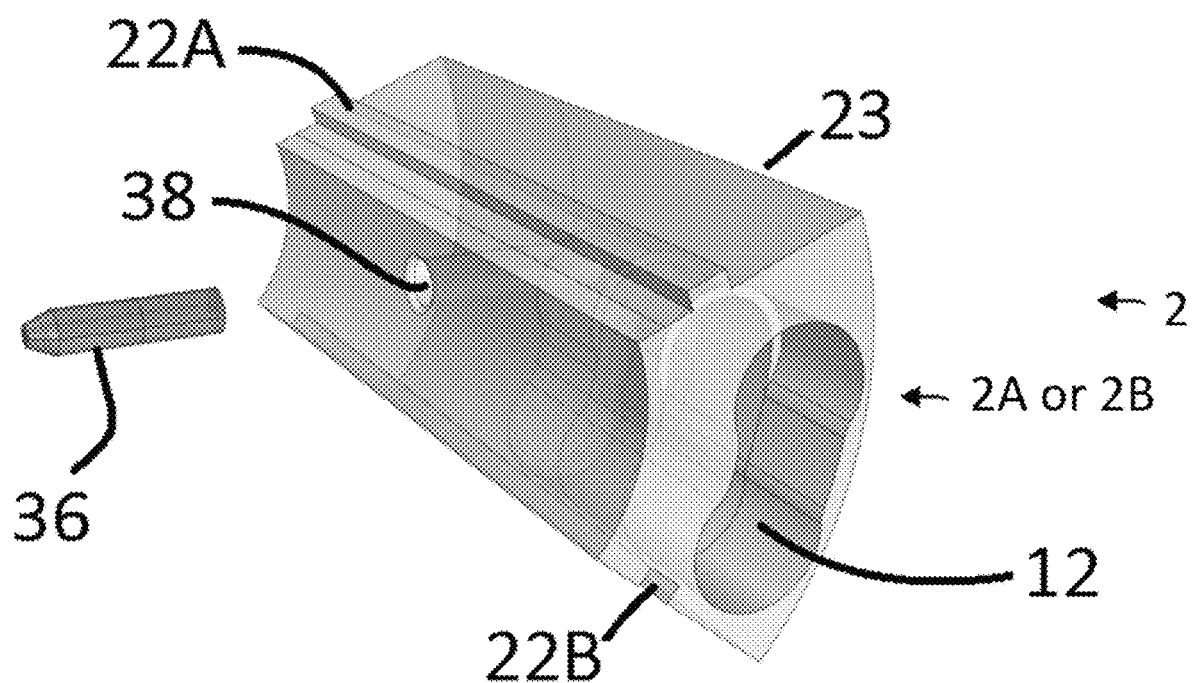
FIG. 42 is a perspective view of the cart 23 for the adapter 2 including a quick connection system 39, according to another embodiment of the invention.

FIG. 42 is a perspective view of the cart 23 for the quick connection system 39, according to another embodiment of the invention.

In other characteristic this embodiment, cart 23 is adapted to connect to the distal end 3B or to the proximal end 3A, according to the embodiment of the invention. In one characteristics of this embodiment, the pin 36 is adapted to enter in the basement 38. In one characteristics of this embodiment, the housing 12 is made to receive the distal end 3B or the proximal end 3A. In one characteristics of this embodiment, the plurality of distal end 3B or proximal end 3A are adapted to engages in the housing 12. In one characteristics of this embodiment, the adapter 2 is rotated by securing the distal end 3B or proximal end 3A in the housing 12.

In the housing 12 the distal end 3B of the elongated rod 3 pushes the pin 36 that enters the groove 24 that holds the tool 8, the way to connect the tool 8 is not limited to that. Generally, the pin 36 remains in the basement 38, is adapted to come out to fit the groove 24.

In this example the cart 23 is adapted for quick connection system 39 by rotation of the connector 37, the elongated rod 3 is engaged in the housing 12 and moves from position "a" to position "b" inside the housing 12 to be fixed in the distal end 3B or to be fixed in the proximal end 3A by the slit 21, the to disconnect the connector 37 with the cart 23 is rotated in the opposite direction.

Figure 43:
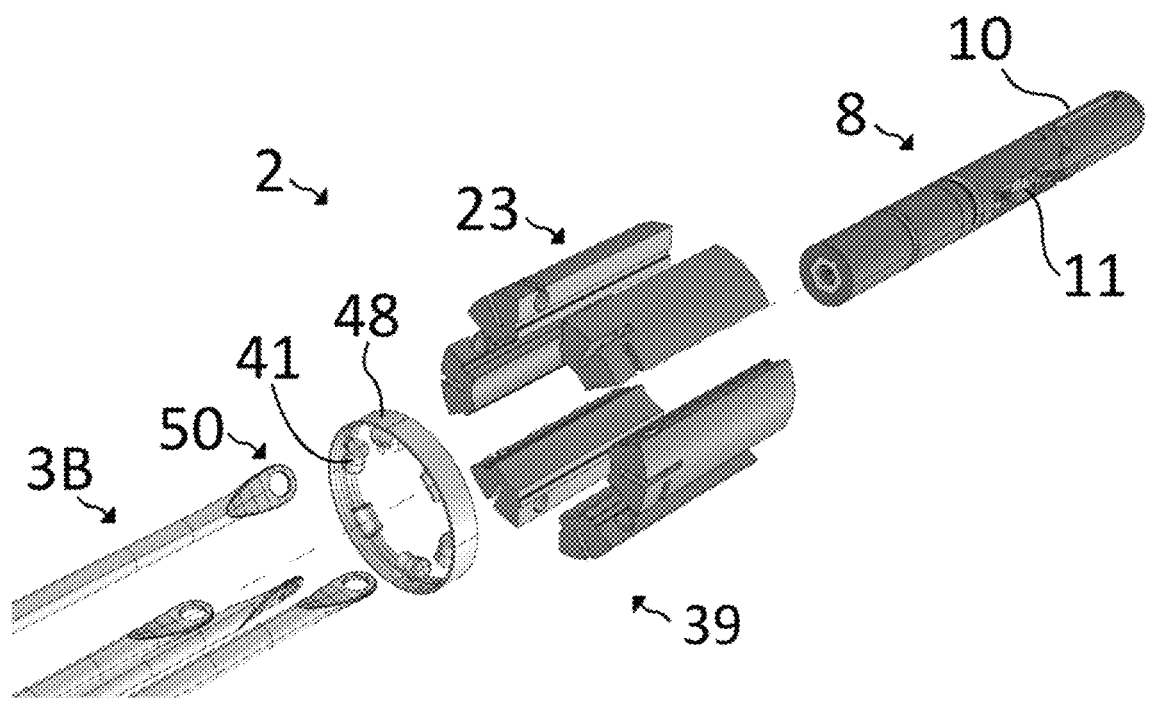
FIG. 43 and FIG. 44 are perspective views of the quick connection system 39A, according to another embodiment of the invention.
Figure 44:
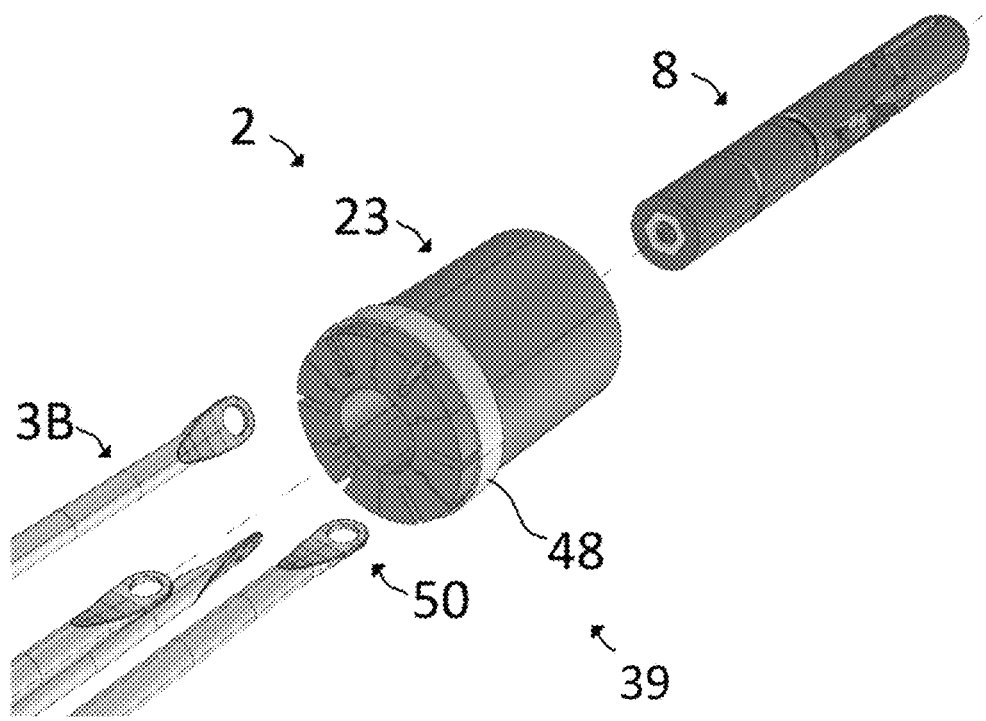

FIG. 43 and FIG. 44 are a perspective view of the quick connection system 39 according to another embodiment of the invention.

In this embodiment, the elongated rod 3 has a hollow 50 in their distal end 3B with a rotating ring 48. A tongue 41 engages inside the hollow 50 by securing the elongated rod 3. In one characteristics of this embodiment, the quick connection system 39B, the elongated rod 3 is released by the rotating ring 48 in the opposite direction.

Figure 45:
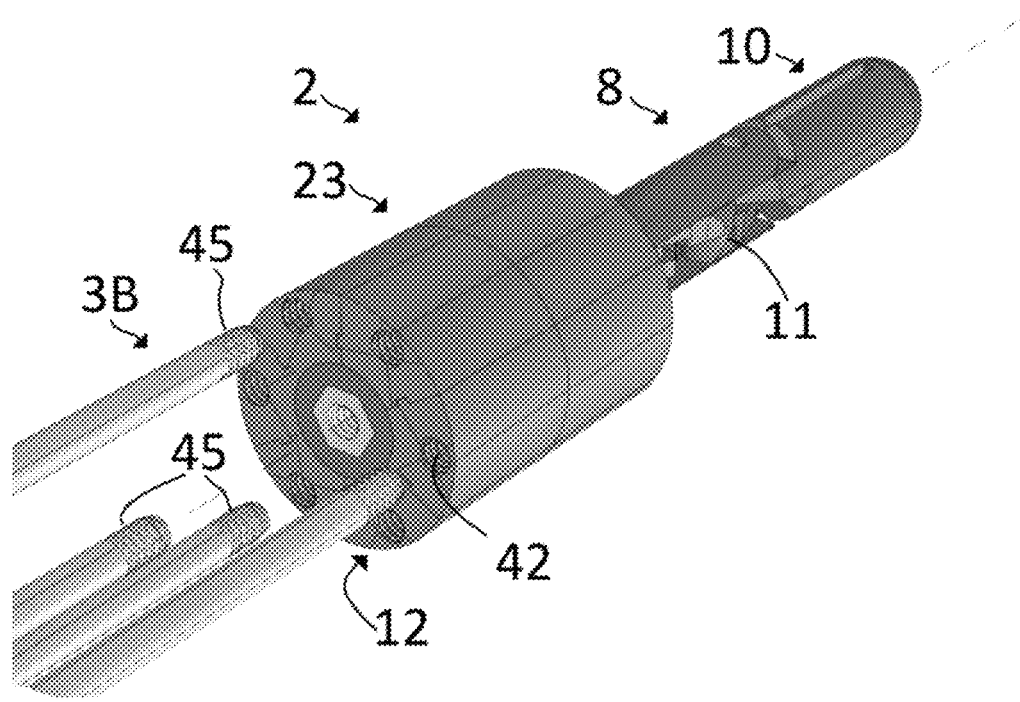
FIG. 45 is a perspective view of the quick connection system 39A, according to another embodiment of the invention.

FIG. 45 is a perspective view of the quick connection system 39, according to another embodiment of the invention.

In this embodiment, the elongated rods 3 are threaded at their distal end 3B.

In one characteristics of this embodiment, the elongated rods 3 connect to the adapter 2 by rotation and the cart 23 have a female thread 42 in the housing 12 for the elongated rod 3 to a screw 45.

Figure 46:
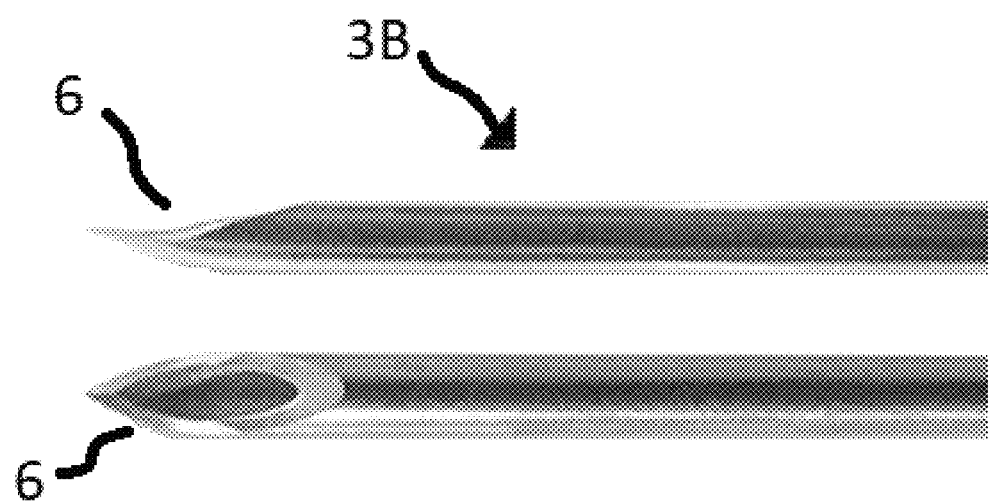
FIG. 46 is a lateral view of the distal end 3B including two piercing tips 6, according to another embodiment of the invention.

FIG. 46 is a lateral view of the distal end 3B including the piercing tip 6, according to another embodiment of the invention.

In one characteristic of some embodiments, the elongated rods 3 have piercing tips 6 to transfix the tissue 25. In other characteristic of this embodiment, the piercing tips 6 are adapted do connect to the functional element 1. In other characteristics of this embodiment, the piercing tips 6 are adapted to leave no scar on the skin. In other characteristics of this embodiment, the piercing tips 6 are adapted to cause minimal trauma to the tissue 25 in order not to leave any scarring in the tissue 25. In other characteristics of this embodiment, the functional element 1 is adapted to connect to the piercing tip 6 elongated rod 3. In other characteristics of this embodiment, each of the elongated rod 3 further includes the piercing tip 6 in the distal end 3B to puncture the tissue 25. In other characteristics of this embodiment, the piercing tip 6 have a sharp tip to easily penetrate the tissue 25 and cause no scars. In other characteristics of this embodiment, the smaller the external diameter of the elongate rod 3, lower is the risk of scarring by perforation.

Figure 47:
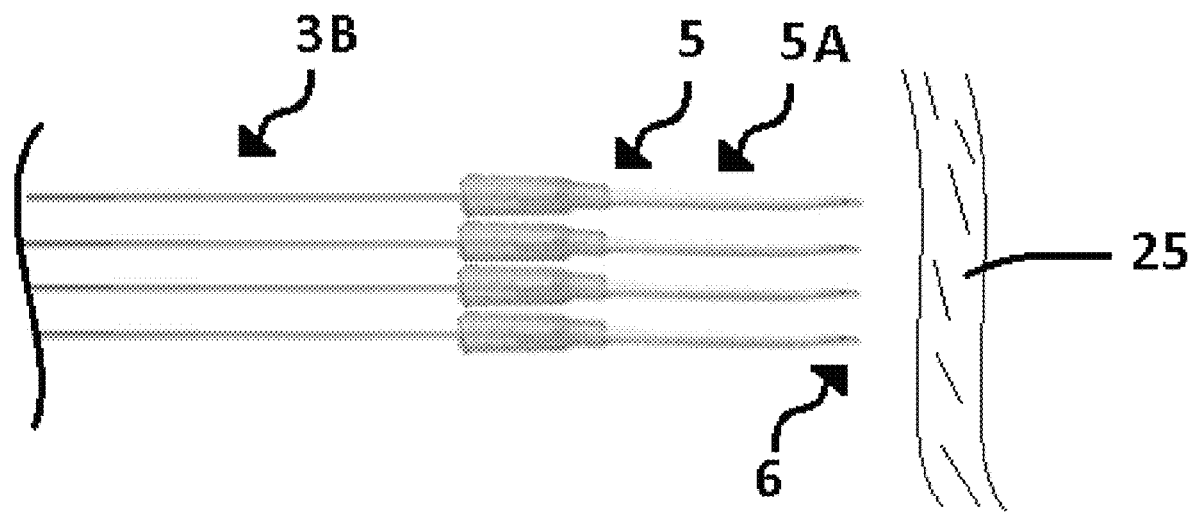
FIG. 47 is a lateral view of the distal end 3B of the elongated rods 3, including four free scar trocars 5 and four cannulas 5A, according to another embodiment of the invention.

FIG. 47 is a lateral view of the distal end 3B of the elongated rod 3, including four free scar trocars 5 and four cannulas 5A, according to another embodiment of the invention.

Figure 48:
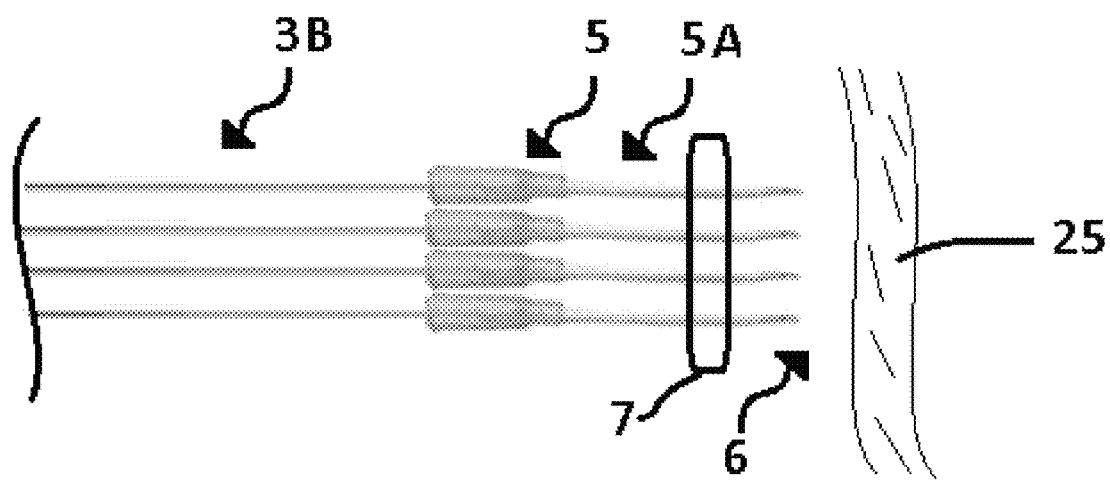
FIG. 48 is a lateral view of the distal end 3B including four free scar trocars 5 and the protector guide 7, according to another embodiment of the invention.

In other characteristics of this embodiment, the surgical device for insertion into the surgical site 26 through a plurality of transfixations 53 in a tissue 25, including: a plurality of elongated rod 3, the elongated rod 3 including a proximal end 3A and a distal end 3B, and the holder 4 connected to the proximal end 3A, further including at least one free scar trocar 5 including piercing tip 6 on the cannulas 5A (FIG. 47; FIG. 48). In other characteristics of this embodiment, the piercing tip 6 has a sharp tip to easily penetrate the tissue 25 and cause no scars. In other characteristics of this embodiment, the smaller the external diameter of the cannulas 5A, lower is the risk of scarring by perforation. In other characteristics of this embodiment, the cannulas 5A have an external diameter thin enough to cause minimal trauma to the tissue 25.

FIG. 48 is a lateral view of the distal end 3B including a plurality of free scar trocars 5 and a protector guide 7, according to another embodiment of the invention. In another characteristic of this embodiment, there is the protector guide 7 on the cannulas 5A. In another characteristic of this embodiment, the protector guide 7 slides along the cannulas 5A. In another characteristic of this embodiment, the protector guide 7 protects the cannulas 5A and directs the insertion of the piercing tip 6 into the tissue 25. In another characteristic of this embodiment, the protector guide 7 drives the insertion of the elongated rod 3 into the tissue 25. In another characteristic of this embodiment, the protector guide 7 holds the cannulas 5A together. In another characteristic of this embodiment, the protector guide 7 is adapted to not delimit out of the cannulas 5A. In another characteristic of this embodiment, the protector guide 7 protects the piercing tip 6 so as not to hurt something. In another characteristic of this embodiment, the protector guide 7 drive the adapted to not slide out of the elongated rod 3. One characteristic of this embodiment is that each of the elongated rod 3 have an outer diameter adapted to cause minimal trauma to the tissue 25, in order to prevent scarring. In one characteristics of this embodiment, the elongated rod 3 outer diameter are thin enough to access the surgical site 26 and cause only minimal trauma to the tissue 25.

Figure 49:
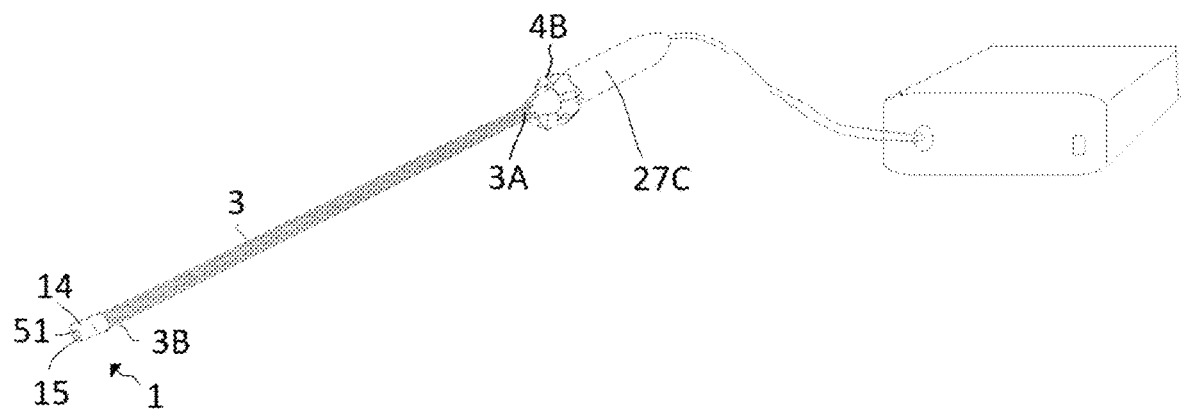
FIG. 49 is a perspective view of a video camera 27C, according to another embodiment of the invention.

FIG. 49 is a perspective view of the invention including the video camera 27C or the camera heard 14, according to another embodiment of the invention.

In other characteristics of this embodiment, there is a surgical device for insertion into the surgical site 26 through a plurality of transfixations 53 in a tissue 25, including: a plurality of elongated rods 3, the elongated rods 3 including proximal ends 3A and distal ends 3B, the holder 4 connected to the proximal ends 3A and the functional element 1 detachably connected to the distal end 3B. In another characteristic of this embodiment, there is further including at least one video camera 27C. In other characteristics of this embodiment, the functional element 1 further including at least one camera head 14.

Figure 50:
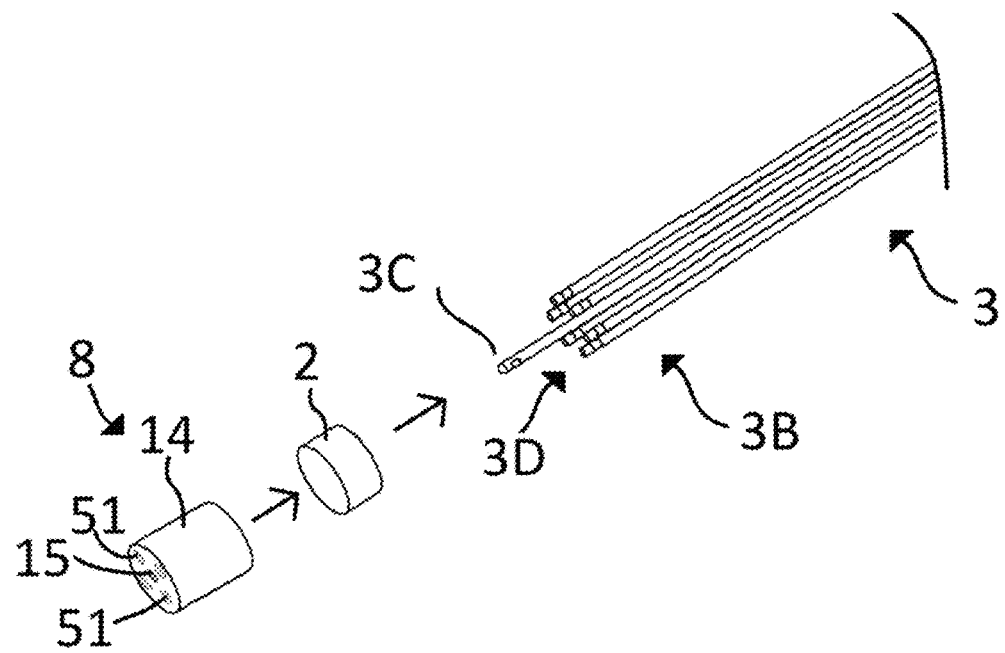
FIG. 50 is a perspective view of the functional element 1 including a camera heard 14, and a perspective view of the distal end 3B, according to another embodiment of the invention.

FIG. 50 is a perspective view of the functional element 1 including a camera heard 14, the adapter 2 and the distal end 3B, according to another embodiment of the invention. In other characteristics of this embodiment, the tool 8 includes the camera heard 14, and the LED 51 to illuminate the surgical site 26.

In one characteristics of this embodiment, the camera head 14 is connectable to the adapter 2 and the adapter 2 is connectable to the distal end 3B. In some embodiments, the optical path 13 extends through the cavity 9A of the command rod 3C and is connectable to the light source 27B to illuminate the surgical site 26. In other characteristics of some embodiment, the camera head 14 electronics includes the imager 29 (it is not shown in the drawing) to produce an electronic image, and a power source (it is not shown in the drawing).

Some embodiment is adapted to operatively connect to at least one external apparatus 27 including: the image processor 27A, the video camera 27C and the light source 27B.

In other characteristics of some embodiment, the electrical wires 52 are adapted to connect the camera head 14 to an external apparatus 27, which includes the image processor 27A. In another characteristic of some embodiment, the image is adapted to be displayed on a video monitor (it is not shown in the drawing). In other characteristics of some embodiment, the image processor 27A includes a control circuitry for processing the electronic image as produced by the imager 29.

In another characteristic of some embodiment, it includes the imager 29 for image pickup. Also, another characteristic of some embodiment, the electrical wires 52 in the cavity 9A communicate the imager 29 with the external apparatus 27A. In another characteristic of some embodiment, the imager 29 is adapted to connect to the electrical wires 52.

In another characteristic of some embodiment, the imager 29 is a solid-state imager. In another characteristic of some embodiments, the imager 29 is a CCD imager. In another characteristic of some embodiments, the imager 29 is a CMOS imager. In other characteristics of some embodiment, the imager 29 and the camera head 14 are configured on a single chip. In other characteristics of some embodiment, the imager 29 produces an electronic image upon being actuated by the external apparatus 27A control circuitry.

A characteristic of some embodiments is that the cavity 9A of the elongated rod 3 includes the first optical path 13A. In another characteristic of some embodiments, the first optical path 13A extends through the elongated rod 3 and through the holder 4.

In other characteristics of some embodiments, the second optical path 13B extends through the elongated rod 3 and through the holder 4. In another characteristic of some embodiments, the second optical path 13B extends from the light source 27B to the camera head 14.

In one characteristic of some embodiments, there is the camera heard 14 including the two imagers 29. In one characteristic of some embodiments, the camera heard 14 including three imagers 29, but the number of imagers 29 in the camera heard 14 are not limited to them. In another characteristic of some embodiments, the second optical path 13B has optical fibers that pass through the cavity 9B. In other characteristics of some embodiments, the second optical path 13 B is implemented with a liquid light guide. In other characteristics of some embodiments, the cavity 9B of the elongated rod 3 is an optical path extending from the light source 27B to the camera head 14.

In other characteristics of some embodiment, the external apparatus 27 includes the light source 27B. In other characteristics of some embodiments, there is a connection from the light source 27B to the existing optical fibers inside the cavity 9B to illuminate the surgical site 26. In one characteristic of some embodiments, there are two optical paths 13 to illuminate the surgical site 26. In one characteristic of some embodiments, there are three optical paths 13 to illuminate the surgical site 26, but the number of optical paths 13 to illuminate the surgical site 26 are not limited to them. In one characteristics of some embodiment, the number of command rod 3C used to illuminate the surgical site 26 is not limited to them.

In another characteristic of some embodiment, the elongated rod 3 includes optical lenses 15 at the functional element 1. In another characteristic of some embodiments, the cavity 9A has optical lenses 15 for transmitting images of the surgical site 26 to the external apparatus 27A. In another characteristic of some embodiment, the cavity 9A has optical lenses 15 for transmitting images of the surgical site 26 to a camera head 14. In another characteristic of some embodiments, it captures the images of the optical lenses 15 of the cavity 9 with the external apparatus 27, which is the video camera 27C, and displays the images of the surgical site 26 on a monitor. In another characteristic of some embodiments, it captures the images of the optical lenses 15 of the cavity 9 with the external camera head 14 which includes the external apparatus 27A.

It will be apparent to one skilled in the art that the invention may be provided including some or all the mentioned features and components without departing from the spirit and scope of the invention. For purposes of comparing some embodiments, certain aspects and advantages of these embodiments are described. Not necessarily all such aspects or advantages are achieved by any particular embodiment. Thus, for example, some embodiments can be carried out in a manner that achieves or optimizes one advantage or group of advantages as described, herein without necessarily achieving other aspects or advantages as can also be described or suggested herein. It will also be apparent to the skilled artisan that the embodiments described above are specific examples of a broader invention which may have greater scope than any of the singular descriptions taught. There may be many alterations made in the descriptions without departing from the spirit scope of the invention. Although, certain preferred embodiments and examples are disclosed, inventive subject matter extends beyond the specifically disclosed embodiments to other alternative embodiments and/or uses, and to modifications and equivalents thereof. Thus, the scope of the claims appended hereto is not limited by any of the particular embodiments described. For example, in any method or process disclosed herein, the acts or operations of the method or process can be performed in any suitable sequence, and they are not necessarily limited to any particular disclosed sequence. Some operations can be described as multiple discrete operations in turn, in a manner that can be helpful in understanding certain embodiments, however, the order of description should not be construed to imply that these operations are order dependent.

I claim:

1. A surgical device for insertion into a surgical site, the surgical device comprising a trocar comprising a plurality of cannulas, each provided with a lumen, wherein each of said cannulas is configured to transfix tissue at a spaced distance from each other, wherein said trocar includes the plurality of said cannulas spaced apart by a distance that establishes the individual lumens, the surgical device further comprising a plurality of elongated rods, each including a proximal end and a distal end; at least one command rod; at least one protector guide configured to guide each of the elongated rods into the individual lumens of the trocar; a detachable holder configured for detachably connecting to the plurality of rods; and an external apparatus comprising a handle; wherein the external apparatus is operatively connectable to the detachable holder; wherein the external apparatus is adapted to be detached and replaced during a surgical procedure without removal the trocar from the tissue; wherein said detachable holder is adapted to be detached and replaced; wherein said protector guide is longitudinally movable with respect to each of the plurality of rods and detachably connectable to said trocar.

2. The surgical device of claim 1, configured to be used as a surgical drain comprising an elastic material.

3. The surgical device of claim 1, further comprising at least one optical path.

4. The surgical device of claim 1, further comprising at least one camera head.

5. The surgical device of claim 1, wherein at least one of said at least one command rod is interchangeable and adapted to be detached and replaced during a surgical procedure without removal of the trocar from the tissue.

6. The surgical device of claim 1, further including a modular functional element configured for detachably connecting each said distal end of the plurality of rods, the modular functional element including an adapter and a tool, wherein said tool is adapted to be disconnected from the adapter and replaced with another tool during a surgical procedure.

7. A surgical device for insertion into a surgical site, the surgical device comprising a trocar comprising a plurality of cannulas; each provided with a lumen, wherein each of said cannulas is configured to transfix tissue at a spaced distance from each other, wherein said trocar includes a plurality of said cannulas spaced apart by a distance, defining the individual lumens; the surgical device further comprising: a plurality of elongated rods, each including a proximal end and a distal end; at least one command rod; a detachable holder configured to connect to the plurality of rods; at least one protector guide configured to guide each of the plurality of elongated rods into the individual lumens of the trocar; an external apparatus comprising a handle; a modular functional element configured to detachably connect each said distal end of the plurality of elongated rods, the modular functional element including a connector, an adapter, and a tool configured to detachably connect the adapter; and a quick connection system, wherein each said proximal end or distal end of the plurality of elongate rods is movable between a first position and a second position within the adapter to facilitate rapid coupling and decoupling of the elongated rods at a single time; wherein said protector guide is longitudinally movable with respect to said plurality of rods and detachably connectable to said trocar; wherein said holder is adapted to be detached and replaced; wherein the external apparatus is operatively connectable to the holder; wherein the external apparatus can be disconnected and replaced with another during the surgical procedure without removal of the trocar from the tissue; wherein said tool is designed for performing a surgical operation.

8. The surgical device of claim 7, wherein the tool includes a surgical stapler.

9. The surgical device of claim 7, wherein the surgical device is adapted for robotic operation.

10. The surgical device of claim 7, wherein the modular functional element is rotatable around one or more axes.

11. The surgical device of claim 7, further comprising a lighting emission diode.

12. The surgical device of claim 7, further comprising at least one motor.

13. The surgical device of claim 7, further comprising at least one battery.

14. The surgical device of claim 7, wherein at least one of said at least one command rod is interchangeable and adapted for replacement during a surgical procedure without removal of the trocar from the tissue.

15. The surgical device of claim 7, further comprising a spinner designed to rotate the modular functional element during a surgical procedure.

16. The surgical device of claim 7, wherein at least one of said at least one command rod is adapted to function as an electric scalpel or an ultrasonic scalpel during a surgical procedure.

* * * * *